(12) United States Patent
Yang et al.

(10) Patent No.: US 9,056,911 B2
(45) Date of Patent: Jun. 16, 2015

(54) ANTIBODY AGAINST CARCINOEMBRYONIC ANTIGEN AND USES THEREOF

(75) Inventors: Zhihua Yang, Beijing (CN); Yuliang Ran, Beijing (CN)

(73) Assignee: Shanghai Haikang Pharmaceutical Tech. & Deve. Co., Ltd., Shanghai (CN)

( * ) Notice: Subject to any disclaimer, the term of this patent is extended or adjusted under 35 U.S.C. 154(b) by 0 days.

(21) Appl. No.: 13/696,251

(22) PCT Filed: Mar. 16, 2011

(86) PCT No.: PCT/CN2011/071840
§ 371 (c)(1),
(2), (4) Date: Nov. 5, 2012

(87) PCT Pub. No.: WO2011/137687
PCT Pub. Date: Nov. 10, 2011

(65) Prior Publication Data
US 2013/0123471 A1    May 16, 2013

(30) Foreign Application Priority Data
May 5, 2010    (CN) .......................... 2010 1 0163052

(51) Int. Cl.
| | | |
|---|---|---|
| *C07K 16/30* | (2006.01) | |
| *C12N 15/00* | (2006.01) | |
| *A61K 51/10* | (2006.01) | |
| *A61K 39/00* | (2006.01) | |

(52) U.S. Cl.
CPC ......... *C07K 16/3007* (2013.01); *C07K 2317/24* (2013.01); *A61K 2039/505* (2013.01); *C07K 2317/14* (2013.01); *A61K 51/1093* (2013.01); *C07K 2317/73* (2013.01)

(58) Field of Classification Search
CPC ........... C07K 16/3007; C07K 2317/14; C07K 2317/24; C07K 2317/73
See application file for complete search history.

(56) References Cited

U.S. PATENT DOCUMENTS

2005/0147614 A1    7/2005    Begent et al.

FOREIGN PATENT DOCUMENTS

WO    WO 03/064611 A2    8/2003

OTHER PUBLICATIONS

Paul, Fundamental Immunology, 3rd Edition, 1993, pp. 292-295.*
Muyldermans, Rev Mol Biotech 2001; 74:277-302.*
Lu et al. Acta Pharmacologica SInica 2005; 26(10): 1259-64.*
Samaranayake et al., Annals Med. 2009; 41:322-331.*
Zhang et al., Cell Res 2007; 17-89-99.*
Chen & Xie, Int'l J. Nanomedicine, 2012; 7:3971-80.*
Hu et al. Nanotechnol 2006; 17:2972-77.*
Ran, Y., et al., "Cloning of variable regions genes of a anti-CEA monoclonal antibody and expression of the human-mouse chimeric antibody," *Journal of Practical Oncology* 16(2):82-86, China Academic Journal Electronic Publishing House, China (2001), with English language abstract.
Zhang, M. et al., "Construction and Screening of the Anti-CEA Single Chain Antibody Gene," *Prog. Biochem. Biophys.* 23(5):470-474, China Academic Journal Electronic Publishing House, China (1996), with English language abstract.
Sato, N., et al., "Intratumoral Distribution of Radiolabeled Antibody and Radioimmunotherapy in Experimental Liver Metastases Model of Nude Mouse," *Journal of Nuclear Medicine* 40(4):685-692, Society of Nuclear Medicine, United States (1999).
Supplementary European Search Report and Search Opinion for European Application No. 11 77 7108, European Patent Office, The Hague mailed Aug. 16, 2013.
Xiong, H., et al., "Expression Vectors for Human-Mouse Chimeric Antibodies," *Journal of Biochemistry and Molecular Biology* 38(4):414-419, Springer, United States (2005).
Yang, Z., et al., "Improved Method for Labelling of Anti-CEA Humanized Chimeric Antibody RCH24 with 131I," *Journal of Labelled Compounds and Radiopharmaceuticals* 48(1):S130, Wiley, England (2005).

* cited by examiner

*Primary Examiner* — Sheela J Huff
*Assistant Examiner* — Jessica H Roark
(74) *Attorney, Agent, or Firm* — Sterne, Kessler, Goldstein & Fox, P.L.L.C.

(57) ABSTRACT

The invention discloses a humanized chimeric monoclonal antibody against carcinoembryonic antigen (CEA), polynucleotides encoding the antibody, expression vectors comprising the polynucleotides, and host cells containing the expression vectors. The invention also discloses uses of the antibody, polynucleotides, vectors and host cells for manufacturing medicaments for diagnosis and/or treatment of tumors.

6 Claims, 16 Drawing Sheets

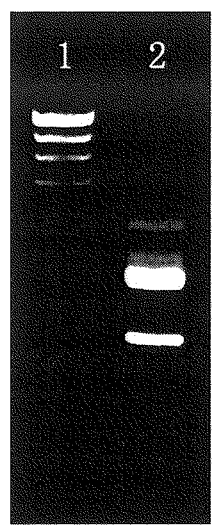
Figure 1: the analysis for the extracted total RNA of the parent mouse monoclonal antibody hybridoma cell using agarose gel electrophoresis.

Figure 2: the analysis for the PCR products of the parent mouse monoclonal antibody VL, VH genes using agarose gel electrophoresis.

VL:

```
              9          18         27         36         45         54
GAC ATC CAG CTG ACC CAG TCT CCA GCA ATC ATG TCT GCA TCT CCA GGG GAG AAG
Asp Ile Gln Leu Thr Gln Ser Pro Ala Ile Met Ser Ala Ser Pro Gly Glu Lys
             63          72         81         90         99        108
GTC ACC ATG ACC TGC AGT GCC AGC TCA AGT GTA AGT TAC ATA CAC TGG TAT CAG
Val Thr Met Thr Cys Ser Ala Ser Ser Val Ser Tyr Ile His Trp Tyr Gln
                    ---------------- CDR1 ------------------
            117         126        135        144        153        162
CAG AAG TCA GGC ACC TCC CCC AAA AGA TGG GTT TAT GAC ACA TCC AAA CTG GCT
Gln Lys Ser Gly Thr Ser Pro Lys Arg Trp Val Tyr Asp Thr Ser Lys Leu Ala
                                                    ----------- CDR2 -----
            171         180        189        198        207        216
TCT GGA GTC CCT GCT CGC TTC AGT GGC AGT GGG TCT GGG ACC TCT TAC TCT CTC
Ser Gly Val Pro Ala Arg Phe Ser Gly Ser Gly Ser Gly Thr Ser Tyr Ser Leu
---
            225         234        243        252        261        270
ACA ATC AGC ACC ATG GAG GCT GAA GAT GCT GCC ACT TAT TAC TGC CAG CAG TGG
Thr Ile Ser Thr Met Glu Ala Glu Asp Ala Ala Thr Tyr Tyr Cys Gln Gln Trp
                                                           ---------------
            279         288        297        306        315
AAT AAT AAC CCA TAC TCG TTC GGA GGG GGG ACC AAG GTG GAG ATC
Asn Asn Asn Pro Tyr Ser Phe Gly Gly Gly Thr Lys Val Glu Ile
- CDR3 ----------------------
```

VH:

```
              9          18         27         36         45         54
CAG GTC CAA CTG CAG CAG TCT GGG GCA GAA CTT GTG AGG TCA GGG GCC TCA ATC
Gln Val Gln Leu Gln Gln Ser Gly Ala Glu Leu Val Arg Ser Gly Ala Ser Ile
             63          72         81         90         99        108
AAG TTG TCC TGC ACA GCT TCT GGC TTC AAC ATT AAA CAC TAC TAT ATG CAC TGG
Lys Leu Ser Cys Thr Ala Ser Gly Phe Asn Ile Lys His Tyr Tyr Met His Trp
                                                    -------- CDR1 -------
            117         126        135        144        153        162
GTG AAA CAG AGG CCT GAA CAG GGC CTG GAG TGG ATT GGA TGG ATT AAT CCT GAG
Val Lys Gln Arg Pro Glu Gln Gly Leu Glu Trp Ile Gly Trp Ile Asn Pro Glu
                                                        ----------------
            171         180        189        198        207        216
AAT GTT GAT ACT GAA TAT GCC CCC AAG TTC CAG GGC AAG GCC ACT ATG ACT GCA
Asn Val Asp Thr Glu Tyr Ala Pro Lys Phe Gln Gly Lys Ala Thr Met Thr Ala
            ------------ CDR2 -----------------------
            225         234        243        252        261        270
GAC ACA TCC TCC AAC ACA GCC TAC CTG CAG CTC AGC AGC CTG ACA TCT GAG GAC
Asp Thr Ser Ser Asn Thr Ala Tyr Leu Gln Leu Ser Ser Leu Thr Ser Glu Asp
            279         288        297        306        315        324
ACT GCC GTC TAT TAC TGT AAT CAC TAT AGG TAC GCC GGA GGG GGT GCT TTG GAC
Thr Ala Val Tyr Tyr Cys Asn His Tyr Arg Tyr Ala Gly Gly Gly Ala Leu Asp
                                       ------------ CDR3 -----------------
            333         342        351        360
TAC TGG GGC CAA GGG ACC ACG GTC ACC GTC TCC TCA 3'
Tyr Trp Gly Gln Gly Thr Thr Val Thr Val Ser Ser
---
```

Figure 3: the nucleotide sequences of the parent mouse monoclonal antibody VL, VH genes obtained by amplification, and amino acid sequences thereof as well as the CDR sequences (the CDRs are underlined).

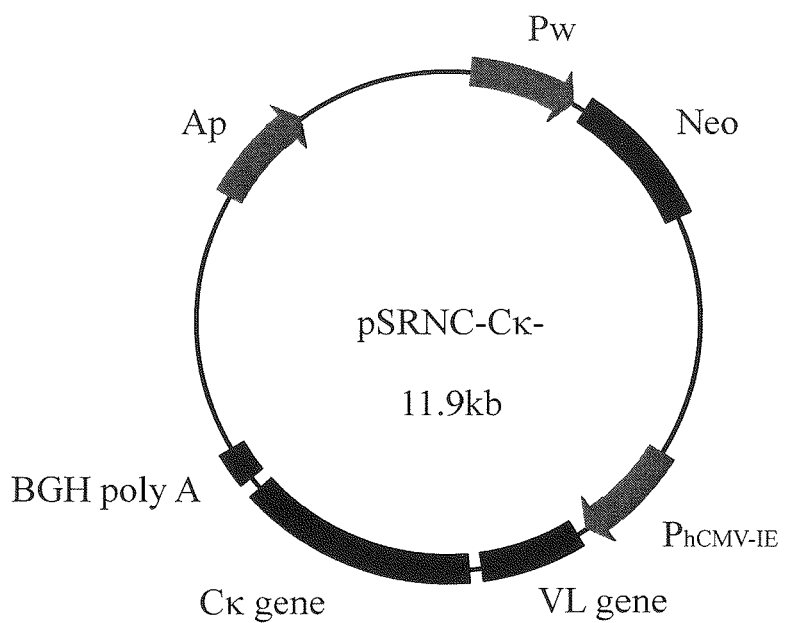
Figure 4: the schematic diagram for the structure of the anti-CEA humanized chimeric antibody light chain eukaryotic expression vector pSRNC-Cκ-CEA.

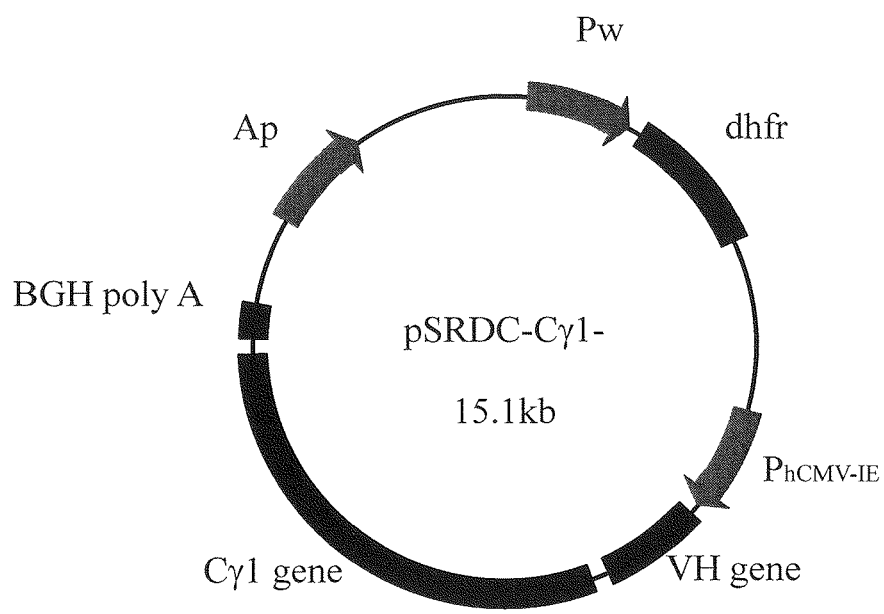
Figure 5: the schematic diagram for the structure of the anti-CEA humanized chimeric antibody heavy chain eukaryotic expression vector pSRDC-Cγ1-CEA.

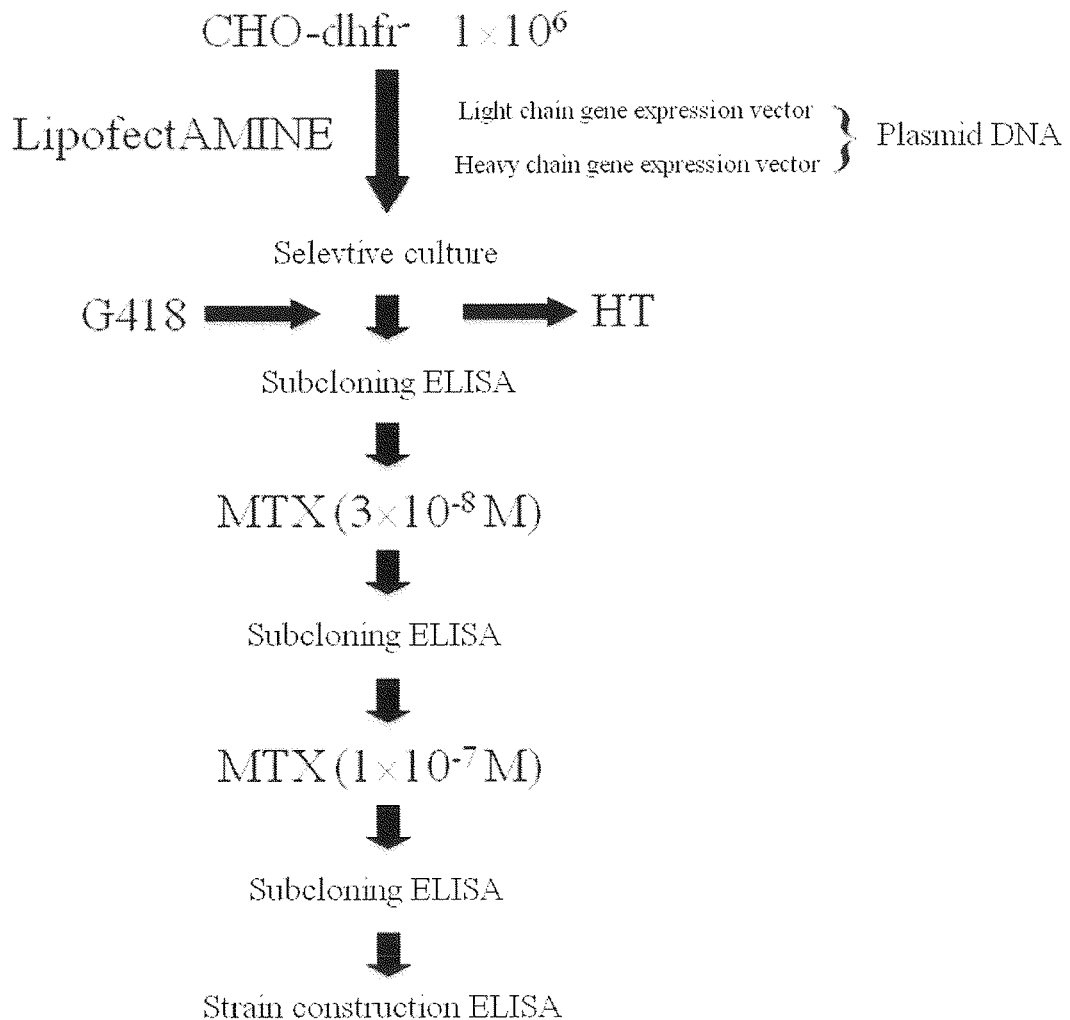
Figure 6: the construction and screening processes for the cell strain that expresses and secrets anti-CEA humanized chimeric antibody in high level.

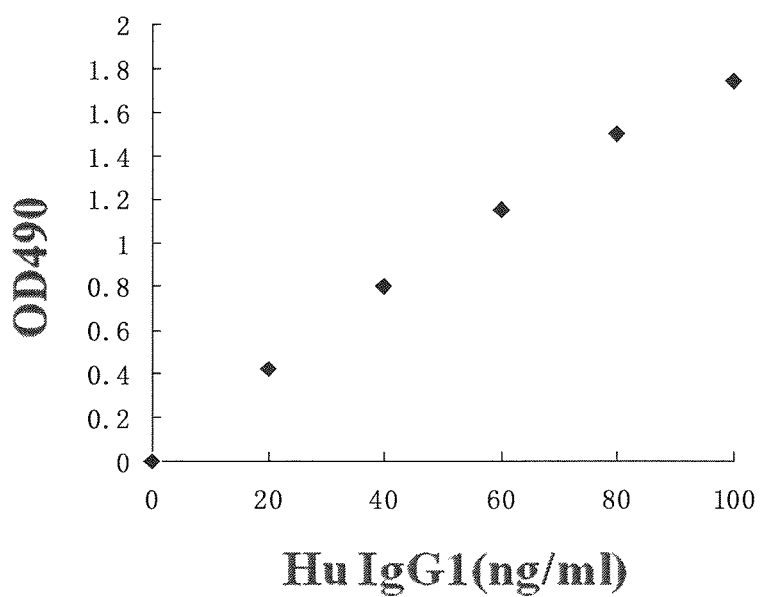
Figure 7: the chimeric antibody content in the supernatant of CHO cell strain that expresses and secrets anti-CEA humanized chimeric antibody measured using ELISA method.

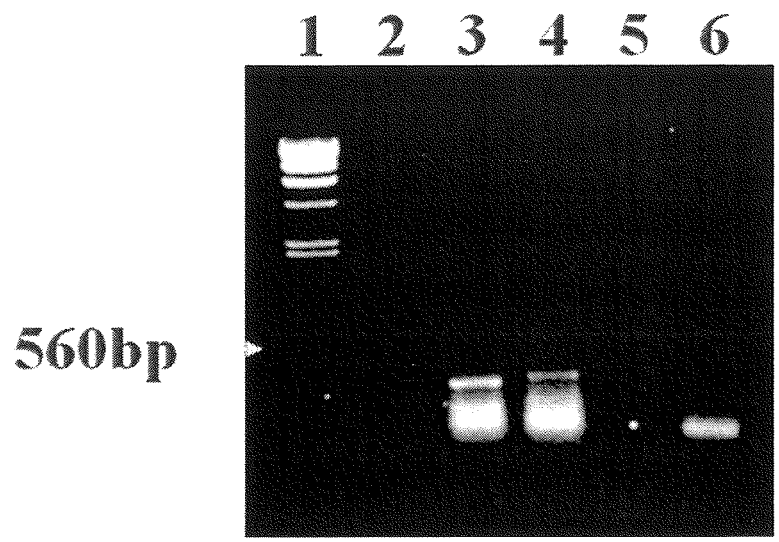
Figure 8: the antigen specificity of anti-CEA humanized chimeric antibody analyzed using RT-PCR.

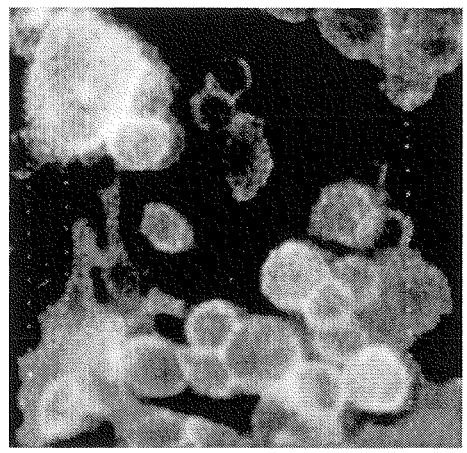
LS180 cells
Figure 9: the antigen specificity of anti-CEA humanized chimeric antibody analyzed using immuno-fluorescence.

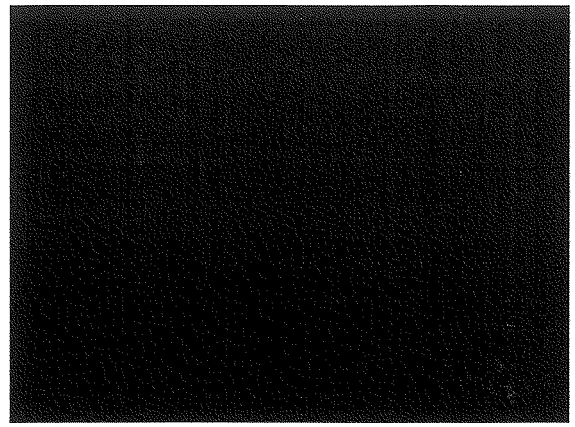
SW1116
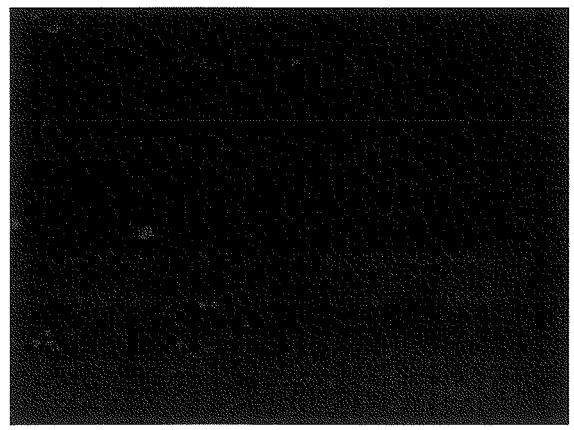
LOVO
Figure 10: anti-CEA humanized chimeric antibody can recognize the CEA antigens on several CEA-expressing cancer cells.

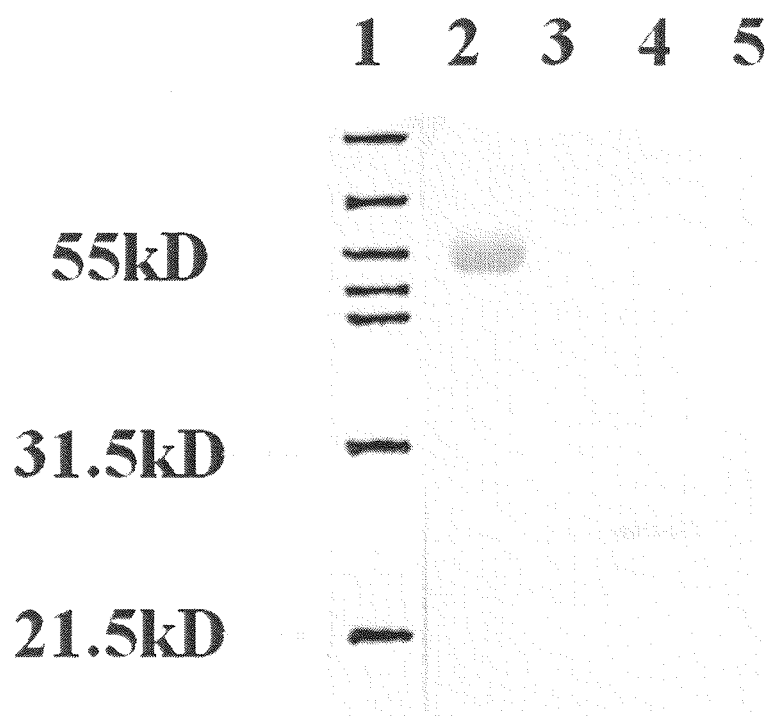
Figure 11: the humanized property of anti-CEA humanized chimeric antibody analyzed using Western-blotting.

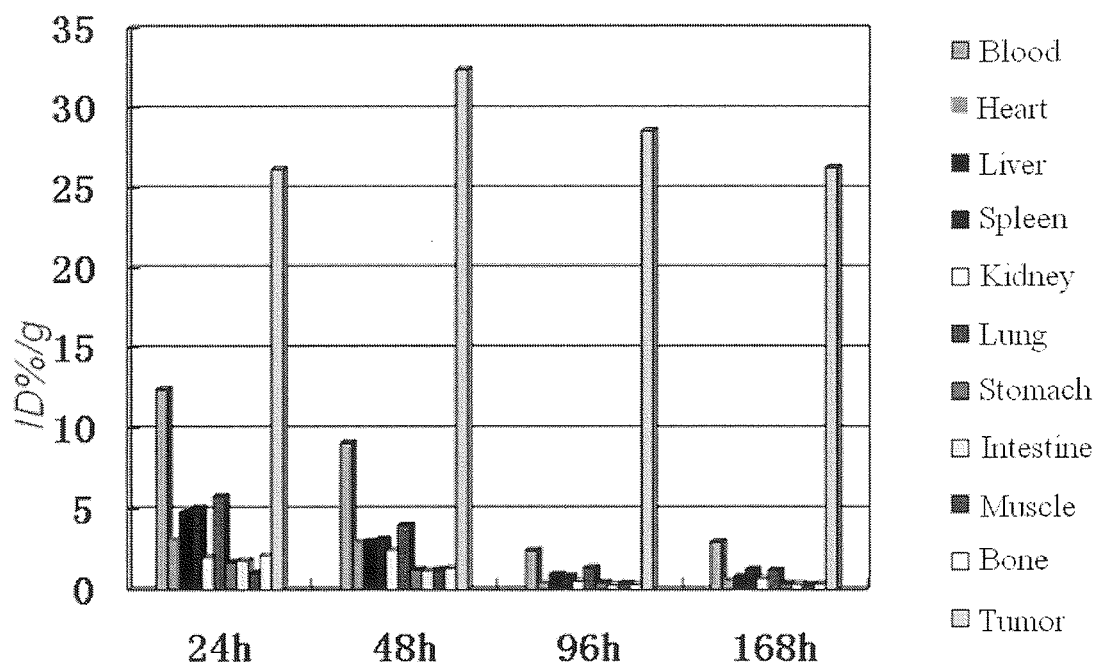
Figure 12. the results of the radioactive dosage uptake analysis expressed as percent per gram tissue (ID%/g) of the anti-CEA humanized chimeric antibody.

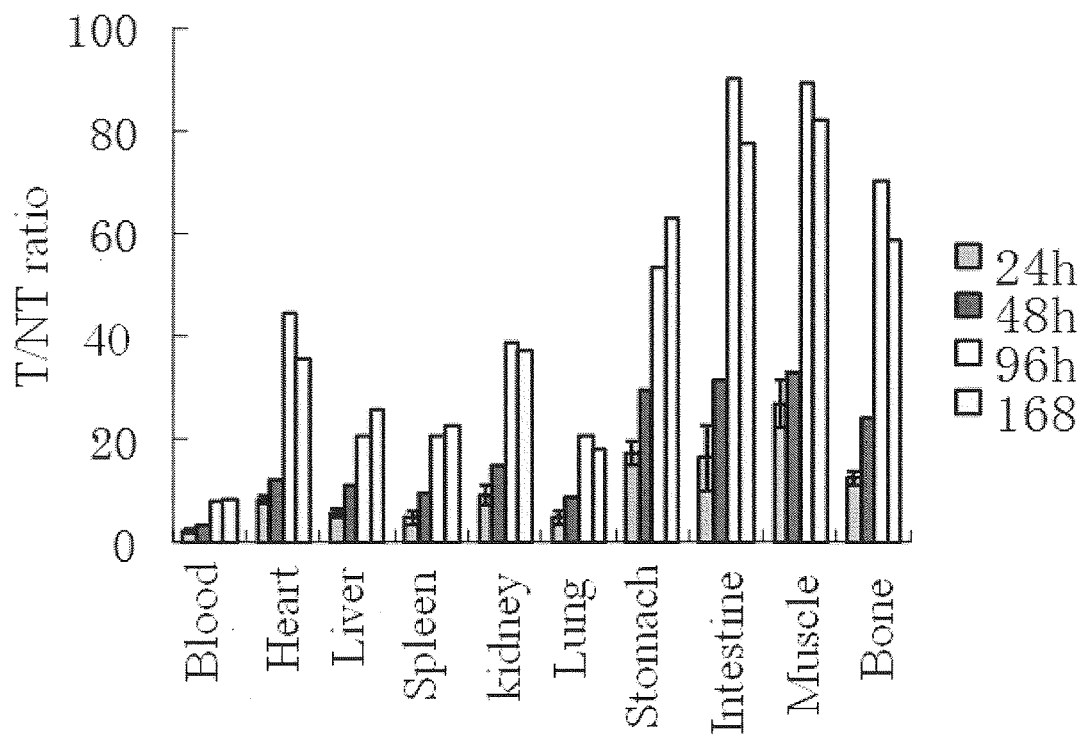
Figure 13: the results of the radioactivity ratio of anti-CEA humanized chimeric antibody between tumor tissue and normal tissue (T/NT).

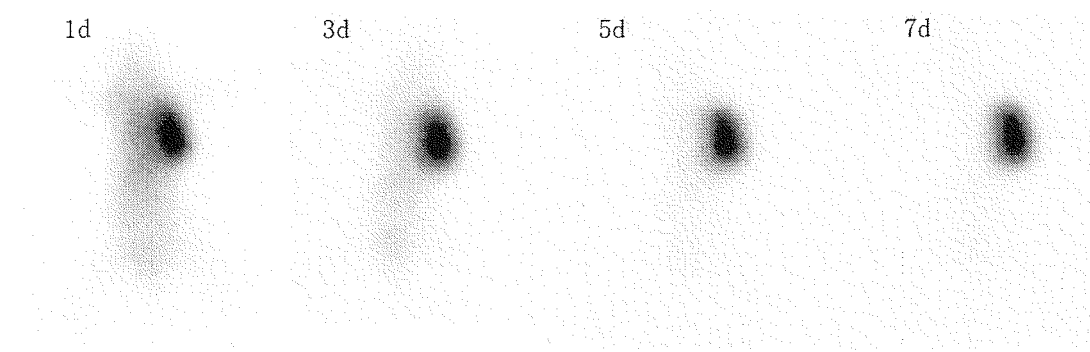
Figure 14: *in vivo* radioactive immuno-imaging of the tumors of CEA positive colon cancer by anti-CEA humanized chimeric antibody.

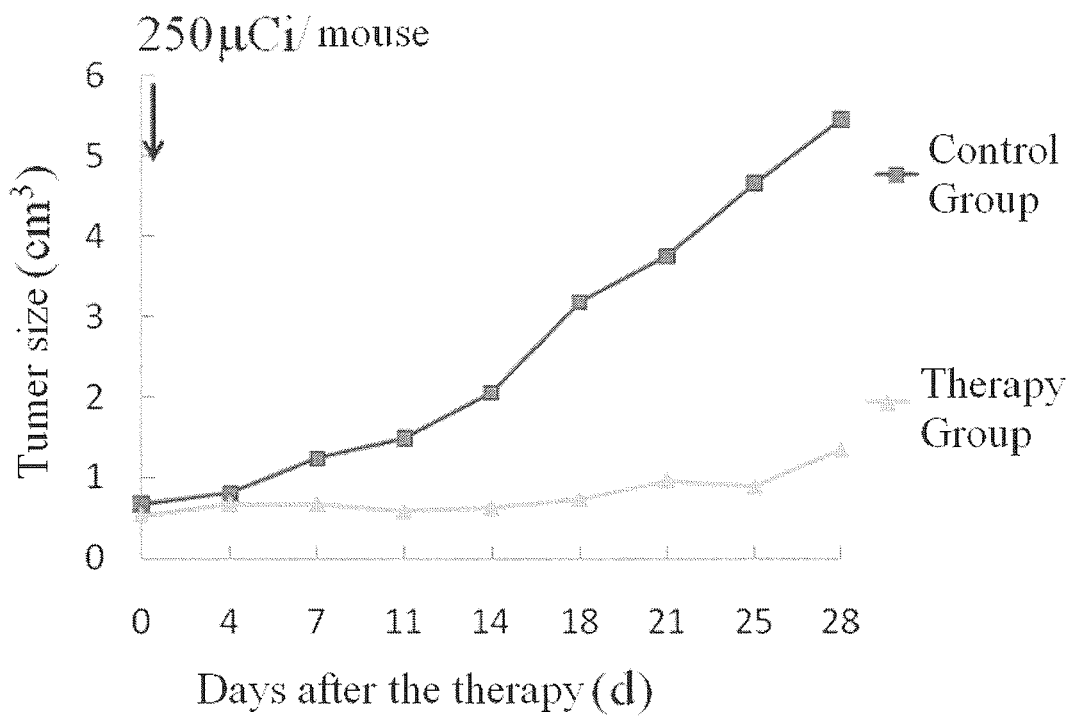
Figure 15: the results of the therapy of the naked mouse transplanted tumor model carrying human colon cancer by a single administration of the conjugate of anti-CEA humanized chimeric antibody and I-13 (growth curve).

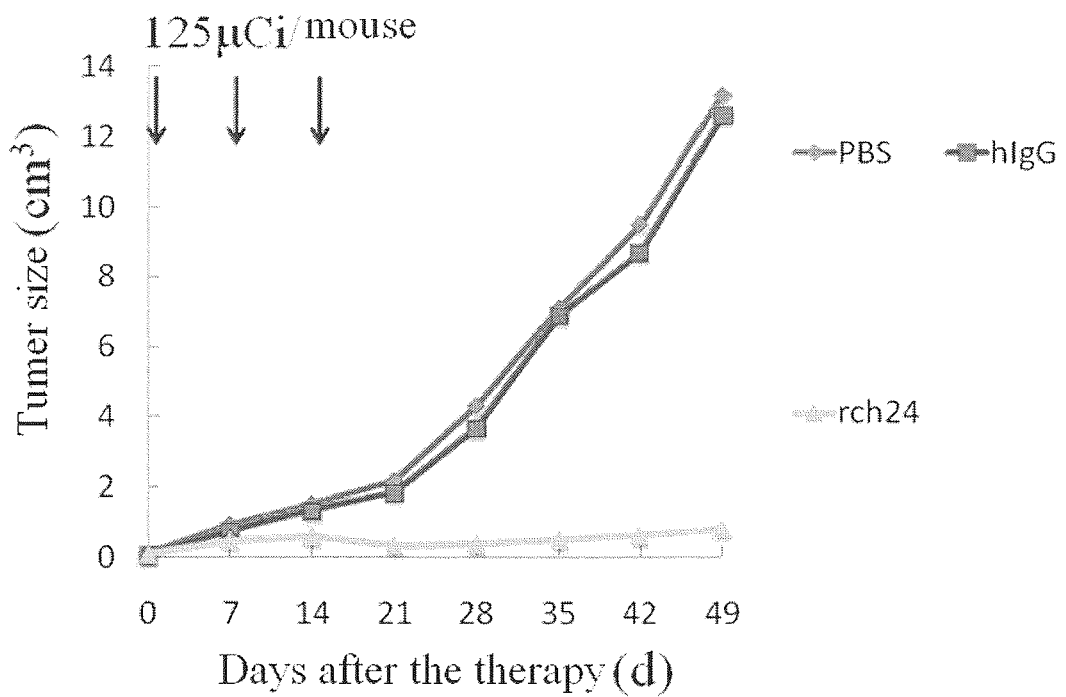
Figure 16: the results of the therapy of the naked mouse transplanted tumor model carrying human colon cancer by multiple administrations of the conjugate of anti-CEA humanized chimeric antibody and I-13 (growth curve).

ANTIBODY AGAINST CARCINOEMBRYONIC ANTIGEN AND USES THEREOF

REFERENCE TO SEQUENCE LISTING SUBMITTED ELECTRONICALLY

The content of the electronically submitted substitute sequence listing, file name 3201_0010000_SequenceListing_22Jan2015_ST25.txt, size 9,524 bytes; and date of creation Jan. 22, 2015, filed herewith, is incorporated herein by reference in its entirety.

TECHNICAL FIELD

The present invention relates to a humanized chimeric antibody against carcinoembryonic antigen (CEA), a polynucleotide encoding the antibody, an expression vector comprising the polynucleotide, and a host cell containing said expression vector, as well as their use in the preparation of an agent or a medicament for diagnosing and/or treating tumor.

BACKGROUND

In 1965, Gold and Fredman from Canada used extract from human colon cancer to immunize rabbit, and the obtained serum was used to examine various human tissues. It was then discovered that the digestive tract tumor originated from human endoderm are strongly positive for staining, and it was also discovered that the digestive tract tissue of 2-6 months old fetus is also positive, and thus such antigen molecule whose expression is positive in digestive tract tumor is named as carcinoembryonic antigen (CEA). Later, it was discovered that the expression of CEA antigen in tumor cells differentiated from endoderm cells is up to hundred folds higher than that of a normal cell, and thus it is an important antigen and marker for various human malignant tumors. CEAs are glycoproteins composed of carbohydrate chain and peptide chain with a molecular weight of about 180-200 kD. Due to the differences in the composition and origin of the carbohydrate chain, the biochemical property and immunogenicity of CEAs exhibit great heterogeneity, diversity, and non-homogenicity, and thus form a relatively big family of macromolecules. CEA molecule has many different antigenic epitopes, and these different epitopes are differently expressed in different normal tissues of adults, fetal organs, and various malignant tumor tissues, and the specificities thereof are also different. Hammarstrom et al. proposed in 1989 that CEA antigenic epitopes can be divided into 5 groups, i.e. Gold 1-5 (Gold classification). It is indicated in studies that the antigenic epitopes of Gold 1-5 groups are respectively located in domains A3, B2, B3, A1, and N of CEA molecules, wherein the A3 and B3 domains have low homology to other CEA related molecules, and they are relatively unique domains of CEA molecules.

CEA is mainly expressed on cell membrane and in cytoplasm of a cell, and it is also expressed in various germ layer tissues of 8-week old embryo. In the tissues of embryo older than 3 months, CEA is mainly expressed in gastrointestinal epithelial tissues; while the expression of CEA in adult tissues is significantly reduced or diminished, with only trace expression on the surface of colon epithelial cells. But CEA is highly expressed in many malignant tumors, including colorectal cancer, stomach cancer, lung cancer, breast cancer, pancreatic cancer, ovarial cancer, cervical cancer, prostate cancer, bladder cancer, gallbladder cancer and esophageal cancer, with a positive rate up to 50-90%. CEA is also highly expressed in metastatic lesions of these malignant tumors, and the expression levels are higher than the primary lesions. Among these tumors, the CEA expression in colorectal cancer is the highest in terms of both positive rate (than 95%) and intensity. CEA is highly expressed in almost all the colorectal cancer tissues, and the expression level and positive rate of CEA in metastatic lesions such as liver metastatic lesions are significantly higher than the primary lesions. It has also been proved in many studies that the expression of CEA in malignant tumors is closely related to the burden, stage, metastasis, and prognosis of tumors. Therefore, CEA has been widely recognized a specific molecular marker for malignant tumors, making it one of the best targets for targeted therapy and diagnosis of tumors.

CEA-positive malignant tumor has a high incidence rate, involving a huge number of patients, making it one of the most threatening diseases for the health of people in the world. For example, colon cancer with high expression of CEA is one of the most commonly seen malignant tumors. The incidence rate of colorectal cancer in European and American developed countries is No. 3 among all the malignant tumors, and the mortality rate thereof in No. 2. The newly developed cases worldwide are more than one million each year, and over 529,000 patients die of colorectal cancer. Each year there are nearly 400,000 newly developed colorectal cancer patients in China, and nearly 200,000 of colorectal cancer patients die due to refractory to treatment. Up to now, FDA has only approved 4 commonly used chemotherapy medicaments for colon cancer: fluorouracie, irinotacan, oxaliplatin, and capecitabine. These currently available chemotherapy medicaments and chemotherapy regimes as postoperative adjunctive treatment can reduce the recurrence rate of colorectal cancer to about 15%, and improve and increase the five-year survival rate to about 10-13%. Antibody targeted medicament is another type of new medicaments that have been developed during the last decade for treating malignant tumors. In the clinical treatment of some hematological system tumors, such as non-Hodgkin lymphoma etc., it has showed significant therapeutic effect, and can increase the five-year survival rate of patients. As for radioactive antibody targeting therapeutic agent using CEA antigens as target, currently no CEA antibody medicament has been approved for clinical use. But two CEA antibody radioactive immunotherapeutic agents have been approved for phase I, II clinical trials. One is $^{131}$I-hMN-14 antibody medicament, i.e. $^{131}$I coupled recombinant humanized anti-CEA antibody hMN-14, which was developed in 1999 by Immunomedics Corp. of USA; and currently the phase II clinical trial for treating drug-resistant metastasis in advanced colorectal cancer has almost been finished, and it has entered the phase III clinical trial. Another anti-human CEA antibody medicament is cT84.66 human/mouse chimeric antibody coupled with radioactive nuclide $^{90}$y, which is developed under the approval of FDA by City of Hope National Medical Center of USA; currently the phase I clinical trial for treating advanced malignant tumors has been finished. However, the above two CEA antibody medicaments still have the some problems, such as the specificity needs to be further improved, the toxic and side effects need to be further reduced; the affinity of antibody is over high, which tends to cause the occurrence of affinity barrier during the targeting radioactive immunotherapy, and thereby significantly influence the therapeutic effect, etc. There is a need for new anti-CEA antibody to overcome the problems of anti-CEA antibodies of the prior art.

It has been concluded in numerous prior studies that, the binding specificity and affinity of an antibody are both predominantly determined by the amino acid sequences of the light chain and heavy chain super variable regions (also referred to as complementary determinant regions, and CDRs in abbreviation). U.S. Food and Drug Administration (FDA) has affirmed in its instructive principles that, all the antibodies of the same type that have the same complementary determinant region belong to one antibody. Accordingly, after obtaining the CDR of one antibody that has clinical therapeutic value, the amino acid sequences of its non-CDR regions can readily be changed through various established and well-known techniques, so as to obtain variants with same or even better biological activities.

SUMMARY OF THE INVENTION

The present invention is based on a parent anti-CEA mouse monoclonal antibody with outstanding CEA binding specificity and appropriate affinity. The sequences of CDR regions thereof have been determined through cloning, identification and gene structure analysis. Corresponding humanized chimeric antibody and its eukaryotic cell expression vector have been constructed, and a cell strain that expresses and secretes the anti-CEA humanized chimeric antibody has been obtained.

The present invention further demonstrates that, besides appropriate affinity which is equivalent to that of the origin mouse monoclonal antibody, said humanized chimeric antibody also has excellent CEA binding specificity and in vivo tumor targeting property, and it can significantly inhibit the growth of colon cancer in many animal models in vivo. Since it is humanized, the toxic and side affects thereof can be reduced when applied to human. The present invention further adopts animal models and experiments like radioactive immuno-imaging to sufficiently prove in vivo that, said humanized chimeric antibody has excellent targeting property for CEA positive tumors, and thus can be used for preparing in vivo diagnosing agent for CEA positive tumors. Furthermore, the present invention also adopts experiments like radioactive immuno-therapy etc. to demonstrate in the body of several animal models that said humanized chimeric antibody has excellent capacity for inhibiting the growth of CEA positive tumors, and thus can be used in the preparation of therapeutic medicament for CEA positive tumors.

Accordingly, the present invention mainly relates to the following aspects:

In the first aspect, the present invention relates to a humanized chimeric monoclonal antibody or its functional variant against carcinoembryonic antigen, wherein the heavy chain of said monoclonal antibody comprises CDR regions as set forth in SEQ ID NOs: 7-9, and the light chain of said monoclonal antibody comprises CDR regions as set forth in SEQ ID NOs: 10-12.

In the second aspect, the present invention relates to an anti-CEA humanized chimeric monoclonal antibody or its functional variant, wherein the amino acid sequence of the light chain of the anti-CEA humanized chimeric monoclonal antibody is SEQ ID NO:1, and the amino acid sequence of the heavy chain is SEQ ID NO:2.

In the third aspect, the present invention relates to a polypeptide having CDR regions that are identical to the CDR regions of said humanized chimeric antibody, and it has biological activity that is equivalent to or higher than the biological activity of said humanized chimeric antibody. It is well known in the art that, both the binding specificity and the affinity of an antibody are primarily determined by the CDR regions. Based on various established, well known prior art techniques, the amino acid sequences of non-CDR regions can be readily changed, so as to obtain a variant having equivalent or higher biological activity.

In the fourth aspect, the present invention relates to a nucleic acid encoding the monoclonal antibody or its variant according to the first or the second aspect, or encoding the polypeptide according to the third aspect. It is well known in the art that, even though the sequence of a nucleic acid is changed, as long as it can finally be translated to an antibody protein comprising the amino acid sequence of SEQ ID NO:1 and the amino acid sequence of SEQ ID NO:2 according to the genetic dogma of triplet codon, it is still a polynucleotide encoding said anti-CEA humanized chimeric antibody. Said nucleic acid can be DNA or RNA.

In the fifth aspect, the present invention relates to an expression vector, which comprises polynucleotide encoding the amino acid sequence of SEQ ID NO:1 and the amino acid sequence of SEQ ID NO:2, and preferably the expression vector is highly expressed in a eukaryotic cell. Preferably, said eukaryotic cell is Chinese hamster ovary cell. In a preferred embodiment, said expression vector is pSRNC-Cκ-CEA as shown in FIG. 4 or pSRDC-Cγ1-CEA as shown in FIG. 5.

In the sixth aspect, the present invention relates to a host cell, which contains the expression vector according to the fifth aspect. In a preferred embodiment, the host cell of the invention is Chinese hamster ovary (CHO) cell, in particular the cell with the deposition No. CGMCC No. 3803.

In the seventh aspect, the present invention relates to use of a therapeutic effective amount of said antibody or polypeptide or a functional variant thereof (e.g. conjugate, fused protein) according to one of aspects 1-3, or of said nucleic acid according to the fourth aspect, or of said vector according to the fifth aspect, or of said host cell according to the sixth aspect, in the preparation of a antitumor medicament. Said tumor is selected from the group consisting of colorectal cancer, stomach cancer, lung cancer, breast cancer, pancreatic cancer, ovarian cancer, cervical cancer, prostate cancer, bladder cancer, gallbladder cancer and esophageal cancer, preferably colorectal cancer. In a preferred embodiment, said antitumor medicament comprises said antibody or polypeptide according to any one of aspects 1-3 coupled to radioactive agent as active ingredient, preferably said radioactive agent is $^{131}$I.

In the eighth aspect, the present invention relates to use of said antibody or polypeptide or a functional variant thereof (e.g. conjugate, fusion protein) according to one of aspects 1-3, or of said nucleic acid according to the fourth aspect, or of said vector according to the fifth aspect, or of said host cell according to the sixth aspect, in the preparation of a tumor diagnostic agent. Said tumor is selected from the group consisting of colorectal cancer, stomach cancer, lung cancer, breast cancer, pancreatic cancer, ovarian cancer, cervical cancer, prostate cancer, bladder cancer, gallbladder cancer and esophageal cancer, preferably colorectal cancer. In a preferred embodiment, said tumor diagnostic medicament comprises said antibody or polypeptide according to any one of aspects 1-3 coupled to radioactive immuno-imaging agent as active ingredient, preferably said radioactive immuno-imaging agent is $^{188}$Re.

DESCRIPTION OF DRAWINGS

FIG. 1 shows the analysis for the extracted total RNA of the parent mouse monoclonal antibody hybridoma cell using agarose gel electrophoresis. Lane 1. molecular weight marker, λ DNA/Hind III. Lane 2. total RNA of the parent mouse monoclonal antibody hybridoma cell.

FIG. 2 shows the analysis for the PCR products of the parent mouse monoclonal antibody VL, VH genes using agarose gel electrophoresis. Lane 1. molecular weight marker, λ DNA/Hind III. Lane 2. the PCR products of the parent mouse monoclonal antibody VL gene. Lane 3. the PCR products of the parent mouse monoclonal antibody VH gene.

FIG. 3 shows the amino acid sequences, nucleotide sequences and CDR sequences of the parent mouse monoclonal antibody VL and VH genes obtained by amplification, wherein the amino acid sequences of VL and VH genes are respectively shown by SEQ ID NO:2 and SEQ ID NO:1, the nucleotide sequences of VL and VH genes are respectively shown by SEQ ID NO:16 and SEQ ID NO:17, and the CDR sequences are underlined.

FIG. 4 shows the schematic diagram for the structure of the anti-CEA humanized chimeric antibody light chain eukaryotic expression vector pSRNC-Cκ-CEA. Pw, attenuated eukaryotic promoter; Neo, aminoglycoside phosphotransferase (neo) gene; PhCMV-IE, human cytomegalovirus immediately-early promoter and enhancer; VL gene, the gene fragment of light chain variable region carrying leader peptide sequence and 5' intron end splicing site sequence; Cκ gene, the κ chain constant region gene fragment of human antibody light chain; BGH poly A, bovine growth hormone poly A tailing site; Ap, ampicillin resistant gene.

FIG. 5 shows the schematic diagram for the structure of the anti-CEA humanized chimeric antibody heavy chain eukaryotic expression vector pSRDC-Cγ1-CEA. Pw, attenuated eukaryotic promoter; dhfr, dihydrofolate reductase (dhfr) gene; PhCMV-IE, human cytomegalovirus immediately-early promoter and enhancer; VH gene, the gene fragment of heavy chain variable region carrying leader peptide sequence and 5' intron end splicing site sequence; Cγ1 gene, the γ1 chain constant region gene fragment of human antibody heavy chain; BGH poly A, bovine growth hormone poly A tailing site; Ap, ampicillin resistant gene.

FIG. 6 shows the construction and screening processes for the cell strain that expresses and secrets anti-CEA humanized chimeric antibody in high level.

FIG. 7 shows the chimeric antibody content in the supernatant of CHO cell strain that expresses and secrets anti-CEA humanized chimeric antibody measured using ELISA method. Wherein, CHO supernatant (1:1000), OD490=1.520, corresponds to 0.08 μg/ml, the concentration of the supernatant stock solution: 0.08×1000=80 μg/ml.

FIG. 8 shows the antigen specificity of anti-CEA humanized chimeric antibody analyzed using RT-PCR. Lane 1. λ DNA/Hind III. Lane 2. 320 bp marker. Lane 3. PCR amplification product of anti-CEA humanized chimeric antibody VL gene. Lane 4. PCR amplification product of anti-CEA humanized chimeric antibody VH gene. Lane 5,6. negative control.

FIG. 9 shows the antigen specificity of anti-CEA humanized chimeric antibody analyzed using immuno-fluorescence.

FIG. 10 shows anti-CEA humanized chimeric antibody can recognize the CEA antigens on several CEA-expressing cancer cells.

FIG. 11 shows the humanized property of anti-CEA humanized chimeric antibody analyzed using Western-blotting. Lane 1. molecular weight marker. Lane 2. chimeric antibody, anti-human IgG Fc-HRP as secondary antibody. Lane 3. mouse monoclonal antibody, anti-human IgG Fc-HRP as secondary antibody. Lane 4. chimeric antibody, anti-human κ chain as primary antibody. Lane 5. mouse monoclonal antibody, anti-human κ chain as primary antibody.

FIG. 12 shows the results of the radioactive dosage uptake analysis expressed as percent per gram tissue (ID %/g) of the anti-CEA humanized chimeric antibody.

FIG. 13 shows the results of the radioactivity ratio of anti-CEA humanized chimeric antibody between tumor tissue and normal tissue (T/NT).

FIG. 14 shows in vivo radioactive immuno-imaging of the tumors of CEA positive colon cancer by anti-CEA humanized chimeric antibody.

FIG. 15 shows the results of the therapy of the naked mouse transplanted tumor model carrying human colon cancer by a single administration of the conjugate of anti-CEA humanized chimeric antibody and I-13 (growth curve).

FIG. 16 shows the results of the therapy of the naked mouse transplanted tumor model carrying human colon cancer by multiple administrations of the conjugate of anti-CEA humanized chimeric antibody and I-13 (growth curve).

DETAILED DESCRIPTION

The antibody variable region of the anti-CEA humanized chimeric antibody of the invention is from an anti-mouse monoclonal antibody C24, which we previously prepared and obtained by immunizing mouse using CEA, and which can be obtained from the hybridoma cell deposited on May 4, 2010 under the deposition number CGMCC NO 3802. Several previous studies (Lu, Baolan. Cheng, Ming. Qiang, Laiying. et al. "The study for the preparation and immunological characteristics of carcinoembryonic antigen monoclonal antibody". *Chinese Journal of Biotechnology*. 1986, 15(2):37) indicate that, this mouse monoclonal antibody has some excellent biological properties suitable for targeting therapy, including having extremely high specificity and appropriate affinity. The monoclonal antibody binds to CEA antigen with high specificity, and can specifically bind to several human tumors in vitro, including stomach cancer, lung cancer, colon cancer, rectal cancer, breast cancer, ovarial cancer, bladder cancer etc., but rarely binds to normal human tissue cells with high specificity. Immunohistochemistry analysis of several thousands of samples demonstrate that, the antibody binds to the aforesaid several tumor tissues with a positive rate of up to 60%-90%, while the positive rate for binding to normal tissues is only between 5%-10%. Furthermore, besides high specificity, another advantage for targeting therapy is that the monoclonal antibody has appropriate affinity. According to the antigen-antibody binding dynamics, when used for targeting therapy, antibody with over high affinity will result in the targeting antibody being absorbed at the surface of tumors, and being prevented from further permeating into the internal of tumors to exert better therapeutic effect. Therefore, antibody with appropriate affinity is more suitable for targeted therapy of tumor. The anti-CEA mouse monoclonal antibody of the invention has appropriate affinity, and the affinity constant is about $1\times10^{-9}$ $M^{-1}$. It can be expected that the humanized antibody thereof will have better therapeutic effects and perspectives in clinical treatment of tumors.

DEFINITION

Monoclonal Antibody

As used herein, the term "monoclonal antibody" refers to antibody obtained from a group of essentially homologous antibodies, i.e. each of the antibodies contained therein will be identical except that there might exist in very little amount some spontaneous mutants. Monoclonal antibody is highly specific antibody against a single target site. Furthermore, contrary to conventional (polyclonal) antibody preparation (which typically contains different antibodies against different determinants (epitopes)), each monoclonal antibody is against one single determinant on the target. Besides its specificity, the advantage of monoclonal antibody is that it can be synthesized through hybridoma culture, and not contaminated by other immunoglobulins. The adjunct "monoclonal" refers to the feature that the antibody is obtained from an essentially homogenous antibody population, but not means that the antibody needs to be produced through any special process. For example, the monoclonal antibody used in the present invention can be isolated from phage antibody library through conventional techniques. The parent monoclonal antibody used according to the present invention can be produced through the hybridoma method first described by Kohler and Milstein, *Nature* 256,495 (1975), or can be produced through recombinant methods.

Complementary Determining Region (CDR)

As used herein, the term "complementary determining region" refers to a sequence in the variable region of binding molecules like immunoglobulin. Typically, it mainly provides antigen binding site that is complementary (in respect of shape and charge distribution) to the recognized epitope on antigen. CDR region can be specific to linear epitope, discrete epitope, or conformational epitope of protein or protein fragment. These epitopes present on protein in their native conformation, or in some cases present on protein in denatured form (e.g. through solubilizing in SDS). Epitope can also be composed of post-translationally modified proteins.

Polynucleotide

As used herein, "polynucleotide" includes deoxyribo-polynucleotide, ribo-polynucleotide, or analogue thereof having essential properties of native ribonucleotide, as long as it can hybridize (just like native nucleotide) with essentially identical nucleotide sequence under stringent conditions, and/or can be translated to identical amino acids just like native nucleotide. Polynucleotide can be a native or heterogeneous structure or full length or subsequence of a regulatory gene. Unless otherwise specified, this term comprises a specific sequence and complementary sequence thereof. Therefore, the term "polynucleotide" as used herein comprises principle chain DNA or RNA that has been modified for stability or other reasons.

Polypeptide

As used herein, the term "polypeptide" can be exchangeably used with "peptide" and "protein", referring to polymers of amino acid residues. This term is used for amino acid polymer, in which one or more amino acid residues are artificial analogues of corresponding native amino acid, and is used for native amino acid polymer. The essential property of such analogue of native amino acid is that, when it is incorporated into protein, the protein can specifically react with an antibody that is stimulated by a protein composed of identical but totally native amino acids. The term "polypeptide", "peptide" and "protein" also comprise modifications, including but not limited to phosphorylation, glycosylation, lipid attachment, sulfidization, γ-carboxylation of glutamic acid residue, hydroxylation, and ADP-ribosylation.

Specific Binding

As used herein, the term "specific binding" mentioned in reference to the interactions between an antibody and its binding partner such as antigen, means that said interaction depends on the presence of a particular structure on the binding partners, such as the presence of antigen determinants or epitopes. In another word, even though said binding partner presents in a mixture of other molecules or organisms, said antibody still preferentially binds or recognizes said binding partner. Said binding can be mediated by covalent or non-covalent interaction or by both of the two interactions. That is to say, the term "specific binding" refers to immuno-specific binding to antigen or fragment thereof and non-immunospecific binding to other antigens. The binding molecule of immuno-specific binding can bind to other peptide or polypeptide in lower affinity, as determined by such as radio-active immuno-analysis(RIA), enzyme linked immunosorbent assay (ELISA), BIACORE, or the assays known in the art. The binding molecule or fragment thereof that immuno-specifically binds antigen can cross-react with related antigen. Preferably, the binding molecule or fragment thereof that immuno-specifically binds antigen does not cross-react with other antigen.

Functional Variant

As used herein, the term "functional variant" refers to a binding molecule, which comprises nucleotide and/or amino acid sequence that modifies one or more nucleotide and/or amino acid when compared to the nucleotide and/or amino acid sequence of the parent binding molecule, but which can still competitively bind to the binding partner (such as CEA) of the parent binding molecule. In another word, the modification in the nucleotide and/or amino acid sequence of the parent binding molecule does not significantly affect or change the binding property of the binding molecule which is encoded by said nucleotide sequence, or which comprises said amino acid sequence, i.e. said binding molecule can still recognize and bind to its target site. Said functional variant can have conserved sequence modification, including substitution, addition, and deletion of nucleotide or amino acid. These modifications can be introduced through standard techniques known in the art, such as site-directed mutagenesis and random PCR mediated mutagenesis, and can comprise native and non-native nucleotide and amino acid.

Conserved amino acid substitution includes the replacement of an amino acid residue by an amino acid residue with similar structure or chemical properties. Amino acid residues families with similar side-chains have been determined. These families include amino acids having basic side chains (such as lysine, arginine, histidine), acidic side chains (such as aspartic acid, glutamic acid), uncharged polar side chains (such as glycine, asparagine, glutamine, serine, threonine, tyrosine, cystine, tryptophane), non-polar side chains (such as alanine, valine, leucine, isoleucine, proline, phenylalanine, methionine), β-branched side chains (such threonine, valine, isoleucine) and aromatic side chains (such as tyrosine, phenylalanine, tryptophane, histidine). A person skilled in the art knows that amino acid residue family classification other than the above can also be applied. Besides, a variant can have non-conserved amino acid substitution, such as replacing an amino acid residue by an amino acid residue with different structure or chemical properties. Similar small change can also include deletion or insertion of amino acid, or both. The instructions for determining that an amino acid residue can be substituted, inserted or deleted without eliminating the immunological activities thereof can be discovered using computer programs known in the art.

A mutation in a nucleotide sequence can be a single mutation (site-mutation) generated in a gene locus, such as transition mutation or transversion mutation, or can be insertion, deletion or change of multiple nucleotides in a single locus. Besides, one or more changes can be generated in any number of loci within a nucleotide sequence. A mutation can be conducted through a proper method known in the art.

Chimeric Antibody

The method for producing a chimeric antibody can be obtained by a person skilled in the art. For example, a light chain and a heavy chain can be respectively expressed in separate plasmids using e.g. an immunoglobulin light chain and an immunoglobulin heavy chain. Then they are purified and assembled in vitro as a complete antibody; method for accomplishing such assembling has been described. See e.g. Scharff, M., *Harvey Lectures* 69:125 (1974). Also see Oi et al., *Bio Techniques* 4(4):214-221 (1986); and Sun et al., *Hybridoma* 5 (1986) Suppl 1:517-20.

The in vitro reaction parameters for forming IgG antibody from recovered isolated light chain and heavy chain have also been described. See e.g. Beychok, S., *Cells of Immunoglobulin Synthesis*, Academic Press, New York, p. 69, 1979. It is also possible to co-express light chain and heavy chain in a same cell so as to accomplish intracellular association of light chain and heavy chain and then link them to form a complete $H_2L_2$ IgG antibody. Such co-expression can be achieved using a same or different plasmids in a same host cell.

Humanized Antibody

The "humanized" form of a non-human (e.g. mouse) antibody is a chimeric immunoglobulin, immunoglobulin chain or fragment thereof (e.g. the Fv, Fab, Fab', $F(ab')_2$ fragment of the antibody, or other subsequence that binds to the target) that contains minimal sequence derived from non-human immunoglobulin. Generally, a humanized antibody at least one, and usually two, of almost the complete variable regions, wherein all, or essentially all, of the CDR regions correspond to those of the non-human immunoglobulin, and all, or essentially all, of the FR regions are those regions of human immunoglobulin consensus sequence. Humanized antibody can also contain at least part of the immunoglobulin constant region (Fc), which usually is at least part of the immunoglobulin constant region of the selected human immunoglobulin template.

Vector

The term "vector" refers to a nucleic acid molecule, in which another nucleic acid can be inserted for introducing it into a host cell to replicate, and express in some cases. In another word, a vector can transfer a nucleic acid molecule connected thereto. Both cloning vector and expression vector are encompassed in the term "vector" used in the present invention. Vector includes but is not limited to plasmid, cosmid, bacteria artificial chromosome (BAC) and yeast artificial chromosome (YAC) and vectors derived from phage or virus of plants or animals (including human). A vector contains the replication origin recognized by a given host; in the case of an expression vector, it also contains promoter and other regulatory regions recognized by the host. A vector containing another nucleic acid molecule can be introduced into a cell through transformation, transfection, or through using the viral entry mechanism. Some vectors can autonomously replicate in the host cell (e.g. a vector having bacterial replication origin can replicate in bacteria). Other vectors can be integrated into the genome of a host when introduced into the host, and thereby replicate together with the genome of the host.

Operably Connected

The term "operably connected" means that two or more nucleic acid elements are usually connected through a physical manner and have functional relationship to each other. For example, if a promoter can initiate or regulate the transcription or expression of the coding sequence, then the promoter and said coding sequence are operably connected, and in this case the coding sequence should be construed as under the "control" of the promotor.

Host

As used herein, the term "host" refers to an organism or a cell, in which a vector such as an expression vector has been introduced. Said organism or cell can be a prokaryotic or eukaryotic organism or cell. It should be understood that this term not only refers to a certain subject organism or cell, but also refers to progenies of this organism or cell. Due to mutations or influence of the environment, some modifications may occur in subsequent generations, and thus such progenies are actually different to the parent organism or cell, but they are still included in the scope of the term "host" as used herein.

Pharmaceutically Acceptable Excipient

"Pharmaceutically acceptable excipient" refers to any inert agent that is combined with active molecule such as medicament, active agent or binding molecule, so as to prepare appropriate or convenient dose form. "Pharmaceutically acceptable excipient" is an excipient that is non-toxic to host at applied dosage and concentration and is compatible to other components of the preparation containing medicament, medicine, or binding molecule.

Therapeutic Effective Amount

The term "therapeutic effective amount" means the amount of the antibody of the invention that can effectively prevent, improve, and/or treat cancer.

Therapy

The term "therapy" refers to therapeutic treatment or prophylactic measure used for curing a disease or for preventing or at least delaying the progress of a disease. The subject to be treated includes subjects that are suffering from cancer and that need prevention for cancer. A subject that is partially or completely recovered from cancer also needs therapy. Prevention includes inhibiting or slowering the progress of cancer or inhibiting or reducing the occurrence, development or progress of one or more symptoms associated with cancer.

In the present description, the term "comprising" means comprising said element, integer, or step, or groups of elements, integers or steps, but not excluding other element, integer, or step, or other groups of elements, integers or steps.

In one aspect, the invention provides a humanized chimeric monoclonal antibody or its functional variant against carcinoembryonic antigen, wherein the heavy chain of said monoclonal antibody comprises CDR regions as set forth in SEQ ID NOs: 7-9, and the light chain of said monoclonal antibody comprises CDR regions as set forth in SEQ ID NOs: 10-12.

In one aspect, the invention provides an anti-CEA antibody or its functional variant, wherein the amino acid sequence of the light chain protein of the antibody comprises or consists of SEQ ID NO:1, and the amino acid sequence of the heavy chain protein comprises or consists of SEQ ID NO:2. In a preferred embodiment of the invention, the anti-CEA antibody is a recombinant or monoclonal antibody. In another preferred embodiment, said antibody is a chimeric or humanized antibody.

In the present application, the term "antibody of the invention" refers to the anti-CEA humanized chimeric monoclonal antibody or its functional variant according to the invention, wherein the heavy chain of said monoclonal antibody comprises the CDR regions as shown in SEQ ID NOs:7-9, and the light chain of said monoclonal antibody comprises the CDR regions as shown in SEQ ID NOs:10-12. Specifically, the amino acid sequence of the light chain protein of the anti-CEA humanized chimeric antibody comprises or consists of SEQ ID NO:1, and the amino acid sequence of the heavy chain protein comprises or consists of SEQ ID NO:2.

The invention also relates to a polypeptide having CDR sequences that are identical to that of said humanized chimeric antibody, and it has biological activity that is equivalent to or higher than the biological activity of said humanized chimeric antibody according to the invention. The term "polypeptide of the invention" refers to a polypeptide having CDR sequence that are identical to that of said humanized chimeric antibody, said polypeptide has biological activity that is equivalent to or higher than the biological activity of said humanized chimeric antibody according to the invention.

In another aspect, the invention relates to nucleic acid encoding the antibody of the invention, which comprises a polynucleotide encoding the antibody or polypeptide of the invention, or a complementary sequence thereof. Said nucleic acid can be DNA or RNA. It is well known in the art that, even though the nucleotide sequence is changed, as long as it can finally be translated to an antibody protein comprising the amino acid sequence of SEQ ID NO:1 and the amino acid sequence of SEQ ID NO:2 according to the genetic dogma of triplet codon, it is still a polynucleotide encoding said anti-CEA humanized chimeric antibody.

In another aspect, the invention provides a recombinant expression vector that can be used for preparing said anti-CEA humanized chimeric antibody. Said vector comprise nucleic acid encoding the antibody of the invention. A vector can be derived from plasmids such as F, R1, RP1, Col, pBR322, TOL, Ti etc.; cosmid; phage such as λ, lambdoid, M13, Mu, P1, P22, Q, T-even, T-odd, T2, T4, T7 etc.; plant virus; or animal virus. A vector can be used for cloning and/or expressing purposes and for gene therapy purpose. A vector that comprises one or more nucleic acid molecules encoding the antibody of the invention operably connected to one or more expression-regulating nucleic acid molecules is also included in the invention. The selection of a vector depends on the recombinantion procedure and the host used. Introducing a vector into a host cell can be achieved through calcium phosphate transfection, virus infection, DEAE-glucan mediated transfection, lipofectamin transfection, or electroporation. A vector can autonomously replicate or can be replicate together with the chromosome into which the vector has been integrated. Preferably, said vector contains one or more selective markers. The selection of said marker can depend on the selected host cell, and it is not critical for the invention and is well known by a person skilled in the art. Said marker includes but is not limited to kanamycin, neomycin, puromycin, hygromycin, zeocin, thymidine kinase gene of herpes simplex virus (HSV-TK), mouse dihydrofolate reductase gene (dhfr). Specifically, in the present invention, the polynucleotides encoding the light chain and heavy chain of the anti-CEA humanized chimeric antibody are recombinantly cloned into two vectors having eukaryotic promotor, respectively. The obtained expression vectors are introduced into eukaryotic host cells. Eukaryotic host cell that expresses the antibody with high yield is obtained through screening, and the supernatant of said host cell's culture contains a great deal of the anti-CEA humanized chimeric antibody protein secreted by the cell. The anti-CEA humanized chimeric antibody protein can be conveniently extracted and prepared from it according to technique methods known in the art. In a preferred embodiment, said expression vectors are respectively pSRNC-Cκ-CEA and pSRDC-Cγ1-CEA, which contain gene of said anti-CEA humanized chimeric antibody and methotrexate stress amplified expression selection marker gene (dhfr), and which can be expressed in Chinese hamster ovary (CHO) cell. In a preferred embodiment, said host cell is Chinese hamster ovary cell CHO.

The invention also provides a host containing one or more copies of said vector. Preferably, said host is a host cell. A host cell includes but is not limited to cell originated from mammalian animals, plants, insects, fungi or bacteria. An expression system using mammalian cells like Chinese hamster ovary (CHO) cell is preferred in the invention. In a preferred embodiment, the invention provides a recombinant host cell (Rcc24), which is Chinese hamster ovary cell containing pSRNC-Cκ-CEA and pSRDC-Cγ1-CEA. Said recombinant host cell is obtained through: stepwise methotrexate stress amplified expression, subcloning the highly-expressing stain screened by expression yield, and finally acclimation in serum-free culture. Said host cell was deposited in China General Microbiological Culture Collection Center on May 4, 2010, with the deposition number CGMCC No. 3803.

According to one aspect of the invention, the anti-CEA humanized chimeric antibody protein can be used in the preparation of a medicament for diagnosing and/or treating human CEA positive tumors. By coupling tracing molecule with the anti-CEA humanized chimeric antibody of the invention, a medicament for diagnosing human CEA positive tumors can be prepared. Said tracing molecule can be radioactive nuclide (e.g. $^{125}$I, $^{111}$In, $^{99}$Tc etc.). Alternatively, other types of molecules that can be detected by clinically acceptable technical means can also be used, such as nano-fluorescence material or far infrared material etc. In a preferred embodiment of the invention, the tracing molecule is radioactive nuclide Rhenium-188. After the tracing molecule is coupled to the anti-CEA humanized chimeric antibody, CEA positive tumors can be precisely diagnosed by radioactive immuno-imaging through γ-camera or imager, with relatively good signal-noise ratio, targeting property and imaging quality.

The antibody of the invention can also be used in the preparation of pharmaceutical composition for the treatment of tumor. Furthermore, some therapeutic agent such as radioactive nuclide can be coupled to the anti-CEA humanized chimeric antibody, to prepare pharmaceutical composition for the treatment of human CEA positive tumors. The "antibody conjugate" as described herein refers to a conjugate that is obtained by coupling a therapeutic substance, such as a radioactive nuclide to the antibody of the invention through various coupling methods known by a person skilled in the art. Said radioactive nuclide includes $^{131}$I, and $^{90}$Y. In a preferred embodiment of the invention, said therapeutic substance is radioactive nuclide iodine-131. After it is coupled to anti-CEA humanized chimeric antibody, radioactive immuno-therapy can be conducted for CEA positive tumors, which can significantly inhibit the growth of tumors, and have excellent therapeutic effect and essentially have no apparent toxic and side effects. In a preferred embodiment, the antibody or antibody conjugate can be used for diagnosing or treating tumors that express CEA, including ovarial cancer, breast cancer, lung cancer, and other CEA positive tumors. In a preferred specific embodiment, said tumor that expresses CEA is colorectal cancer. Based on existing clinical diagnosing techniques, a person skilled in the art can detect the CEA content in the serum of patient, and determine whether the patient's tumor is CEA-positive, and can readily choose appropriate tumor type to be treated. A person skilled in the art should also understand that, the aforesaid pharmaceutical composition can also contain pharmaceutically acceptable excipient.

Said anti-CEA humanized chimeric antibody can be administered to patients as a medicament through conventional administration routes, including but not limited to parenteral administration, such as transvenous, infusion, topical administration etc. Appropriate dose depends on several parameters, including the method for administration and the subject to be treated and the tolerance level. It is clear that $^{131}$I labeled anti-CEA humanized chimeric antibody can significantly inhibit the growth of human colorectal cancer in a dose-dependent manner. The preferred dose is 12.5 mCi/kg, and the treatment was conducted twice with a ten-day interval.

The present invention will be further illustrated through the following examples, but any example or combination thereof should not be construed as a limitation for the scope or embodiment of the invention. The scope of the invention is defined by the attached claims. Based on the present description in combination with common knowledge in the art, a skilled person can clearly understand the scope defined by the claims.

The Deposition Information of Biological Materials

The mouse hybridoma cell line C24 that produces the parent mouse monoclonal antibody was deposited in China General Microbiological Culture Collection Center (CGMCC, Datun Road in Chaoyang District of Beijing, the Institute of Microbiology, Chinese Academy of Sciences) on May 4, 2010, with the deposition number CGMCC No. 3802.

The CHO cell line Rcc24 that produces humanized chimeric monoclonal antibody was deposited in China General Microbiological Culture Collection Center (CGMCC, Datun Road in Chaoyang District of Beijing, the Institute of Microbiology, Chinese Academy of Sciences) on May 4, 2010, with the deposition number CGMCC No. 3803.

EXAMPLES

Example 1

The Cloning and Sequencing of Genes for the Chimeric Antibody

Using gene cloning method, the genes for the light and heavy chain variable regions in the monoclonal antibody of parent anti-CEA mouse were cloned, and nucleotide sequence analysis was conducted.

Method for amplifying the genes for the variable regions of the parent anti-CEA mouse monoclonal antibody: Extraction of the total RNA from mouse monoclonal antibody hybridoma cell C24 was conducted as follows according to the instructions of Trizol reagent (Gibco). $1\times10^7$ mouse monoclonal antibody hybridoma cells were collected and centrifuged at 10000 rpm for 1 min. After pipetting and discarding the supernatant, 1 ml Trizol was added to sufficiently lyse the cells. After being kept still at room temperature for 3-5 min, 0.2 ml chloroform was added. After reversing and blending, the sample was centrifuged at 4° C. 12000 rpm for 10 min, then about 0.6 ml of the supernatant was transferred into a new centrifuge tube, and 0.5 ml isopropanol was added. After reversing and blending, the sample was kept still at room temperature for 5-10 min, and then centrifuged at 4° C. 12000 rpm for 10 min. After discarding the supernatant, the sample was washed once with 75% ethanol, air-dried, and then 50 μl ddH$_2$O was added to dissolve the precipitate. The synthesis of the first chain of mouse monoclonal antibody hybridoma cell cDNA was conducted using MMLV-reverse transcriptase (Gibco) according to the instruction provided by the manufacturer. 4 μl 5×buffer, 10 mM DDT (Promega), 10 μg total RNA, dNTPs at the final concentration of 0.5 mM (Promega), Oligo d(T)15 at the final concentration of 10 μg/ml (Promega), 40 u RNasin (Promega), 200 u(U) MMLV-reverse transcriptase (Gibco) were added into a 20 μl system, which was then blended. The sample was incubated at 37° C. for 1 h, and then in boiling water for 5 min to deactivate the reverse transcriptase. Amplification of the mouse monoclonal antibody light and heavy chain variable region genes was conducted using High-fidelity DNA polymerase Taq (Promega)+ Pfu DNA polymerase (Promega) in a 100 μl reaction system containing 10×buffer 10 μl, 10 mM dNTP 2 cDNA 20 μl, 50 pmol of each of the amplification primers. The surface of the reaction system was covered with paraffin oil after blending. After incubated in 95° C. water bath for 5 min, 1-2 u of Taq+Pfu DNA polymerase was added through the paraffin oil, and the following cycle was initiated: 30 cycles of 94° C. for 1 min, 55° C. for 1 min, and 72° C. for 1 min, and 72° C. for 10 min in the last cycle. PCR primers: primers for the amplification of the light chain variable region: PVL5: 5'-GACAT TCAGC TGACC CAGTC TCCA-3' (SEQ ID NO:3); PVL3: 5'-GTTAG ATCTC CAGCT TGGTC CC-3' (SEQ ID NO:4). Primers for the amplification of the heavy chain variable region: PVH5: 5'-AGGTS MARCT GCAGS AGTCW GG-3' (S=C/G, M=A/C, R=A/G, W=A/T) (SEQ ID NO:5); PVH3: 5'-TGAGG AGACG GTGAC CGTGG TCCCT TGGCC CCAG-3' (SEQ ID NO:6).

0.7% non-denaturing agarose gel electrophoresis was conducted to analyze the total RNA. The sizes of 18S RNA and 28S RNA were correct, the brightness ratio was about 1:2, and the bands were distinct, indicating that the extracted total RNA was relatively complete (FIG. 1). Oligo d(T)15 was used as primer to synthesize the first chain of cDNA, and this cDNA was used as template to conduct PCR. By using light chain primers PVL5 and PVL3, a gene fragment of light chain variable region of about 320 bp was amplified; and by using heavy chain primers PVH5 and PVH3, a gene fragment of heave chain variable region of about 360 bp was amplified. Blank control without template showed no amplified band (FIG. 2). The sizes of the amplified variable region gene fragments were in conformity with the sizes of variable region genes of normal antibodies.

The cloning, sequencing, and gene structure analysis of the genes of the parent anti-CEA mouse monoclonal antibody light chain, heavy chain variable region: The gene fragments of the parent anti-CEA mouse monoclonal antibody light chain variable region were amplified in high amount. After isolation and recovery using Glass Milk adsorption method, the fragments were subjected to Pvu II and Bgl II double-digestion, and then cloned into the corresponding site of cloning vector pRGWL. In all the 153 transformed clones, 24 clones were randomly picked for screening, and 6 recombinant clones were obtained. Three VL gene recombinant clones were selected for nucleotide sequence analysis. The nucleotide sequence and the deduced amino acid sequence were shown in FIG. 3. The sequences of the 3 clones were identical, indicating that the cloned antibody light chain variable region genes were indeed the parent anti-CEA mouse monoclonal antibody light chain variable region genes. One clone was randomly picked from the three clones, and was named as pRGWH-0502. It can be seen from the comparison with Kabat's data that, VL (SEQ ID NO:2) of the parent anti-CEA mouse monoclonal antibody belongs to mouse κ light chain VI subgroup. Light chain CDR1-3 sequences (SEQ ID NOs:10-12) were shown in FIG. 3. The gene fragments of the parent anti-CEA mouse monoclonal antibody heavy chain variable region were amplified in high amount. After isolation and recovery using Glass Milk adsorption method, the fragments were subjected to Pst I and BstE II double-digestion, and then cloned into the corresponding site of cloning vector pRGWH. In all the 364 transformed clones, 24 clones were randomly picked for screening, and 18 recombinant clones were obtained. Three VH gene recombinant clones were selected for nucleotide sequence analysis. The nucleotide sequence and the deduced amino acid sequence were shown in FIG. 3. The sequences of the three clones were identical, indicating that the cloned antibody heavy chain variable region gene was indeed the parent anti-CEA mouse monoclonal antibody heavy chain variable region gene. One clone was randomly picked from the 3 clones, and was named as pRGWL-0504. It can be seen from the comparison with Kabat's data that, VH (SEQ ID NO:1) of the parent anti-CEA mouse monoclonal antibody belongs to mouse heavy chain II(B) subgroup. Heavy chain CDR1-3 sequences (SEQ ID NOs:7-9) were shown in FIG. 3. Specifically, the sequences of SEQ ID NOs:7-12 are:

SEQ ID NO: 7
His Tyr Tyr Met His

SEQ ID NO: 8
Trp Ile Asn Pro Glu Asn Val Asp Thr Glu Tyr Ala
Pro Lys Phe Gln Gly

SEQ ID NO: 9
Tyr Arg Tyr Ala Gly Gly Gly Ala Leu Asp Tyr

SEQ ID NO: 10
Ser Ala Ser Ser Ser Val Ser Tyr Ile His

SEQ ID NO: 11
Asp Thr Ser Lys Leu Ala Ser

SEQ ID NO: 12
Gln Gln Trp Asn Asn Asn Pro Tyr Ser

Example 2

The Construction of the Genes and Expression Vectors for Anti-CEA Humanized Chimeric Antibody By using gene cloning and DNA recombination methods, the variable region genes of the parent anti-CEA mouse monoclonal antibody were recombined into a vector containing regulatory sequences and human antibody constant region genes, to construct the genes of anti-CEA humanized chimeric antibody and a eukaryotic expression vector containing said genes.

PCR amplification of the variable gene fragments carrying the regulatory sequences: The PCR amplification was conducted using a high-fidelity DNA polymerase, i.e., Taq+Pfu DNA polymerase, in a 100 μl reaction system containing 10×buffer 10 μl, 10 mM dNTP 2 μl, plasmid 1 μg, 50 pmol of each amplification primers. After blending, the surface of the reaction system was covered with paraffin oil. After incubated in 95° C. water bath for 5 min, 1-2 u of Taq+Pfu DNA polymerase was added through the paraffin oil, and the following cycle was initiated: 20 cycles of 94° C. for 1 min, 55° C. for 1 min, 72° C. for 1 min, and 72° C. for 10 min in the last cycle.

The construction and identification of the eukaryotic expression vector of anti-CEA humanized chimeric antibody: The recombinant cloning plasmids pRGWL-0502 and pRGWH-0504 obtained and identified in Example 1 were used as templates, and primers PVLS and PVNP (for light chain) and PVHS and PVNP (for heavy chain) with BamH I and Not I restrictive sites for the purpose of cloning were used for PCR amplification, to amplify the VL and VH sequences of the parent anti-CEA mouse monoclonal antibody carrying a leader peptide sequence and 5' end splicing site. By PCR amplification, the VL fragment of the parent anti-CEA mouse monoclonal antibody carrying the leader peptide sequence and 5' end splicing site was amplified from the recombinant plasmid for light chain, and the size of the VL fragment was about 500 bp; the VH fragment of the parent anti-CEA mouse monoclonal antibody carrying the leader peptide sequence and 5' end splicing site was amplified from the recombinant plasmid for heavy chain, and the size was about 700 bp. The PCR products were isolated and recovered by using Glass Milk method, and then digested using BamH I and Not I. According to the conventional DNA recombinantion procedure described in "Molecular Cloning", the VL fragment was cloned into corresponding site in pSRNC-Cκ, and the VH fragment was cloned into corresponding site in pSRDC-Cγ1 so as to obtain the complete eukaryotic expression vectors of the anti-CEA humanized chimeric antibody gene. After VL and VH fragments were respectively linked into expression vectors pSRNC-Cκ and pSRDC-Cγ1, twelve clones were respectively picked for screening. Through enzyme digestion, 9 light chain and 7 heavy chain recombinant clones were obtained. After enzyme digestion by BamH I and Not I, corresponding VL and VH fragments were identified, demonstrating that complete anti-carcinoembryonic antigen monoclonal antibody gene and the eukaryotic expression vector thereof were successfully constructed. Through two rounds of nucleotide sequencing, it was proved that the variable region gene sequences in the anti-carcinoembryonic antigen monoclonal antibody eukaryotic expression vectors pSRNC-Cκ-CEA and pSRDC-Cγ1-CEA were completely identical to the variable region gene sequences contained in pRGWL-0502 and pRGWH-0504, respectively.

The structure of the anti-CEA humanized chimeric antibody eukaryotic expression vector: The anti-CEA humanized chimeric antibody eukaryotic expression vector system contains two separate expression vectors, i.e., the light chain eukaryotic expression vector pSRNC-Cκ-CEA and the heavy chain eukaryotic expression vector pSRDC-Cγ1-CEA, the schematic diagram of their structures were shown in FIGS. 4 and 5.

Example 3

Expression by CHO Cells Transfected with the Expression Vector of Anti-CEA Humanized Chimeric Antibody CHO-dhfr⁻ cells (stored in our lab) were cultured in DMEM complete growth medium with 10% FBS, 0.03 mmol/L hypoxanthine (H), 0.003 mmol/L thymidine deoxynucleoside (T), 0.1 mmol/L proline (Pro), 0.1 mmol/L glycine (Gly), 100 u/ml penicillin/streptomycin, 2 mmol/L glutamine under the conditions of 5% $CO_2$, 37° C. Passage was routinely performed at a ratio of 1:10 every 3-4 days. The above cell culture reagents were purchased from Gibco corp. Using gene transfection method, Lipofect AMINE reagent (Gibco) was used for transfection. The cells were transfected with the expression vectors of anti-CEA humanized chimeric antibody, and then screened by culturing in a medium without H, T, Gly. After the clones were formed, selective medium containing 200 μg/ml G418 (Gibco) was used for culture to conduct screening. As results, 4 μg of each of the light chain and heavy chain chimeric antibody gene expression vectors were used to transfect CHO-dhfr⁻ cells. Formation of clones was observed after about 10 days, and all together about 350 clones were counted. The supernatant of the culture of the pooled resistant clones was measured as $OD_{490}$=1.622 by using indirect ELISA method, while $OD_{490}$ of the negative control CHO-dhfr⁻ supernatant was only 0.063, indicating that there was anti-CEA humanized chimeric antibody expression in the supernatant of the transfected cells.

TABLE 1

Detection of anti-CEA humanized chimeric antibody in the cell culture after transfection by ELISA

| Sample | $OD_{490}{}^a$ | $OD_{490}{}^b$ | $OD_{490}{}^c$ |
|---|---|---|---|
| supernatant 60 hours after the infection | 0.900 ± 0.005 | 0.900 ± 0.005 | 1.848 ± 0.021 |
| pooled supernatant of the clones (1:10) | 0.643 ± 0.004 | 0.637 ± 0.003 | 1.622 ± 0.011 |
| supernatant of clone 1C5 (1:10) | 0.916 ± 0.017 | 0.913 ± 0.006 | 1.880 ± 0.010 |
| PBS (0 ng/ml human IgG1) | 0.076 ± 0.003 | 0.070 ± 0.001 | — |
| 20 ng/ml human IgG1 | 0.480 ± 0.007 | 0.452 ± 0.004 | — |
| 40 ng/ml human IgG1 | 0.895 ± 0.005 | 0.874 ± 0.002 | — |
| 60 ng/ml human IgG1 | 1.130 ± 0.014 | 1.050 ± 0.009 | — |
| supernatant of CHO-dhfr⁻ | 0.081 ± 0.003 | 0.075 ± 0.002 | 0.063 ± 0.002 |

$^a$coated with goat-anti-human IgG polyclonal antibody;
$^b$coated with goat-anti-human κ chain polyclonal antibody;
$^c$coated with human CEA antigen.

Example 4

Screening for Strains that can Highly Express Anti-CEA Humanized Chimeric Antibody by Methotrexate (MTX) Amplification The transformed CHO cells were cultured in DMEM complete growth medium (Gibco) with 10% FBS, 100 u/ml penicillin/streptomycin, 2 mmol/L glutamine under the conditions of 5% $CO_2$, 37° C. Passage was routinely performed at a ratio of 1:10 every 3-4 days. The screening method of methotrexate (MTX) amplification was used to screen highly-expressing strains. Cell clones with expression of the anti-CEA humanized chimeric antibody in supernatants were sequentially cultured in complete media respectively containing $3 \times 10^{-8}$M and $10^{-7}$M methotrexate (MTX) (Sigma), for amplifying expression under stress. After each round of the amplifying expression, subcloning was conducted by limited dilution, so as to select the clone with highest yield (FIG. 6).

Clone 1C5 (with the yield of chimeric antibody up to 0.41 μg/ml), which was obtained in the first screening after transfecting the anti-CEA humanized chimeric antibody expression vector into CHO-dhfr⁻ cells, and which can highly-effectively express anti-CEA humanized chimeric antibody, was cultured in a medium containing $3 \times 10^{-8}$ M methotrexate (MTX) (Sigma). After successive culture for about 30 days, it was observed that the cell modality and growth rate recovered to normal, and the cells adapted to $3 \times 10^{-8}$M of MTX. The expression yield of chimeric antibody was 10.4 μg/ml. After subcloning, the clone 2B2 with highest chimeric antibody yield was selected, and the yield of chimeric antibody was 16 μg/ml. After passage at a ratio of 1:5, the clone 2B2 was then cultured in a complete media containing $10^{-7}$ M MTX. After the cells adapted, the yield of chimeric antibody was 32 μg/ml. After subcloning, the clone 3B2 with highest chimeric antibody yield was selected, and through a preliminary detection, the chimeric antibody yield was as high as 80 μg/ml (FIG. 7).

Example 5

The Preparation of Cell Strain Adapted to Serum-Free Suspension Culture and Capable of Producing Anti-CEA Humanized Chimeric Antibody Method of decreasing serum was used to prepare cell strain (adapted to serum-free suspension culture), so as to obtain cell strains (adapted to serum-free suspension culture) that can express and secret anti-CEA humanized chimeric antibody in high level.

rCHO RCC-24 cells (i.e. clone 3B2), which adherently grew when cultured in a medium containing serum and expressed and secreted anti-CEA humanized chimeric antibody in high-effectively, was first cultured in culture flask in DMEM complete growth medium (Gibco) containing 5% serum. After they adapted and showed a stable growth, the medium was sequentially replaced with complete growth medium respectively containing 2%, 1%, 0.5%, 0.25% serum in the same way. After they adapted and showed a stable growth, the medium was finally replaced with serum-free medium, i.e., CHO-S-SFM II growth medium (Gibco). At this time, most of the cells had lost the property of adherent growth, and the culture essentially turned to be a semi-suspension. After the cells adapted and showed a stable growth, the cells were then cultured in shaking flasks at 80-100 rpm, and the cells were forced to grow in suspension. After the cells adapted and showed a stable growth, the obtained new cells, which are capable of growing in serum-free suspension culture and effectively expressing and secreting the anti-CEA humanized chimeric antibody, were named as rCHO RCC-24(SF) cell line.

Example 6

The Identification of the Specificity, Humanized Property, and In Vivo Targeting Property of the Anti-CEA Humanized Chimeric Antibody 1. Identification of the Specificity of the Anti-CEA Humanized Chimeric Antibody:

RT-PCR method was performed, wherein the extraction of cell total RNA was conducted according to the instruction of Trizol reagent, specifically as described in Example 1. The synthesis of the first chain of cDNA was conducted using MMLV-reverse transcriptase (Promega) according to the instruction of the manufacturer, specifically as described in Example 1. In PCR amplification experiment, the method for amplifying the variable region genes from the cDNA of a cell was as described in Examples. The results indicated that, after sequencing, the light chain and heavy chain variable region genes (FIG. 8) amplified from rCHO RCC-24(SF) cell line were identical to the light chain and heavy chain variable region genes of the original parent anti-CEA mouse monoclonal antibody, and thus the anti-carcinoembryonic antigen monoclonal antibody can maintain the specificity of the parent anti-CEA mouse monoclonal antibody, and specifically bind to CEA.

ELISA method was performed, wherein 1 μg/ml CEA was used for coating the ELISA plate. After the sample was added for reactions, then goat-anti-human IgG Fc fragment-HRPELISA antibody (Sigma) (not cross-reacting with mouse Ig) or goat-anti-mouse IgG Fc fragment-HRP ELISA antibody (Sigma) (not cross-reacting with human Ig) were added; after incubation and color generation, the OD490 value was measured. Subsequently, human CEA antigens were used to for coating the ELISA plate, and then goat-anti-human IgG Fc fragment-HRP was used as secondary antibody to conduct direct ELISA. Both the anti-CEA humanized chimeric antibody in the supernatant of transformed cells and the anti-CEA humanized chimeric antibody purified by Protein A affinity chromatography column can bind to the CEA antigen used for coating, and can be recognized by goat-anti-human IgG Fc fragment polyclonal antibody, exhibiting strong positive reaction. The non-transformed CHO-dhfr⁻ cell culture supernatant and the parent mouse monoclonal antibody exhibited negative reaction. When using goat-anti-mouse IgG Fc fragment-HRP as secondary antibody, both the non-transformed CHO-dhfr⁻ cell culture supernatant and the purified anti-CEA humanized chimeric antibody exhibited negative reaction, while the parent mouse monoclonal antibody exhibited positive reaction. Irrelevant antibody human IgG1 were negative for both cases. It was demonstrated that the expressed anti-CEA humanized chimeric antibody can specifically bind to CEA antigens, and had the same antigen-binding specificity as the parent mouse monoclonal antibody.

TABLE 2

Direct ELISA for analyzing the antigen-binding specificity of anti-CEA humanized chimeric antibody

| Sample | $OD_{490}{}^a$ | $OD_{490}{}^b$ |
|---|---|---|
| anti-CEA humanized chimeric antibody (purified, 100 ng/ml) | 2.571 ± 0.032 | 0.072 ± 0.000 |
| human IgG1(100 ng/ml) | 0.079 ± 0.007 | 0.077 ± 0.005 |
| parent mouse monoclonal antibody (100 ng/ml) | 0.072 ± 0.003 | 2.636 ± 0.043 |
| PBS control | 0.070 ± 0.001 | 0.072 ± 0.001 |
| CHO-dhfr⁻ cell supernatant | 0.076 ± 0.002 | 0.073 ± 0.002 |

$^a$goat-anti-human IgG Fc fragment-HRP was used as secondary antibody;
$^b$goat-anti-mouse IgG Fc fragment-HRP was used as secondary antibody Competitive inhibition experiment was performed, wherein 1 μg/ml of CEA antigen was used for coating the ELISA plate (Biodesign). 2.5 ng/well of irrelevant mouse monoclonal antibody (prepared by ourselves) or 2.5 ng/well of the parent anti-CEA mouse monoclonal antibody C50 (prepared by ourselves) and different concentrations of anti-CEA humanized chimeric antibody were added. After incubation at 37° C., then goat-anti-mouse IgG-HRP ELISA antibody (Sigma) was added; the OD490 value was measured after the reaction, and the competitive inhibition rate thereof was calculated. Competitive inhibition rate was calculated according to the following formula: and irrelevant antibody human IgG1 control was also used.

$$\text{competitive inhibition rate} = \frac{OD490 \text{ of mouse monoclonal antibody alone} - OD490 \text{ after chimeric antibody being added}}{OD490 \text{ of mouse monoclonal antibody alone}} \times 100\%$$

The results of competitive inhibition experiment are shown in the following table, negative control irrelevant antibody human IgG1 and the parent anti-CEA mouse monoclonal antibody reaction showed no competitive inhibition effect (the competitive inhibition rate was −12.80%). When the ratio between anti-CEA humanized chimeric antibody and the parent anti-CEA mouse monoclonal antibody was 2:1, then significant competitive inhibition can occur for the binding between the parent anti-CEA mouse monoclonal antibody and the antigen. With the increase in the concentration of the chimeric antibody, the amount of binding product between the parent anti-CEA mouse monoclonal antibody and the antigen decreased, the OD490 thereof gradually decreased, and the competitive inhibition rate increased. When the ratio was 32:1, the competitive inhibition rate can reach up to 40.85%. This indicated that anti-CEA humanized chimeric antibody and parent anti-CEA mouse monoclonal antibody can both bind to the same epitopes of the CEA antigen, and thereby demonstrated that the anti-CEA humanized chimeric antibody and parent anti-CEA mouse monoclonal antibody have same antigen-binding specificity.

TABLE 3

Using competitive inhibition ELISA to examine the specificity of anti-CEA humanized chimeric antibody

| Sample | $OD_{490}$ | Inhibition rate (%) |
|---|---|---|
| 2.5 ng parent anti-CEA mouse monoclonal antibody CHO-dhfr⁻ cell supernatant | 1.394 ± 0.044 0.000 ± 0.003 | — 0 |
| 2.5 ng parent anti-CEA mouse monoclonal antibody 0 + 80 ng human IgG1 | 1.573 ± 0.010 | −12.8 |
| 2.5 ng parent anti-CEA mouse monoclonal antibody + 2.5 ng anti-CEA humanized chimeric antibody | 1.359 ± 0.024 | 2.5 |
| 2.5 ng parent anti-CEA mouse monoclonal antibody + 5 ng anti-CEA humanized chimeric antibody | 1.166 ± 0.006 | 16.36 |
| 2.5 ng parent anti-CEA mouse monoclonal antibody + 10 ng anti-CEA humanized chimeric antibody | 0.997 ± 0.008 | 28.52 |
| 2.5 ng parent anti-CEA mouse monoclonal antibody + 20 ng anti-CEA humanized chimeric antibody | 0.903 ± 0.041 | 35.22 |
| 2.5 ng parent anti-CEA mouse monoclonal antibody + 40 ng anti-CEA humanized chimeric antibody | 0.884 ± 0.009 | 36.59 |
| 2.5 ng parent anti-CEA mouse monoclonal antibody + 80 ng anti-CEA humanized chimeric antibody | 0.825 ± 0.047 | 40.85 |

Immuno-fluorescence test was performed, wherein colon cancer cell LS180 (purchased from ATCC) that can express CEA in high level was used as target cell, and anti-CEA humanized chimeric antibody was added. After incubation at 37° C., goat-anti-human IgG-FITC fluorescent secondary antibody (Sigma) was then added, fluorescent microscope was used for observation after the reaction, and irrelevant antibody control was used as control. The results in FIG. 9 indicated that, anti-CEA humanized chimeric antibody can recognize the CEA antigens on colon cancer cell LS180 that can express CEA in high level.

Immuno-fluorescence test was performed, wherein several CEA-expressing cancer cells SW1116, LOVO (purchased from ATCC) were used as target cells, and anti-CEA humanized chimeric antibody was added. After incubation at 37° C., goat-anti-human IgG-Cy5 fluorescent secondary antibody (Sigma) was then added; fluorescent microscope was used for observation after the reaction, and irrelevant antibody control was used as control. The results (FIG. 10) indicated that, monoclonal antibody against carcinoembryonic antigen can recognize CEA antigens on CEA-expressing cancer cells.

2. Identification of the Humanized Property of the Anti-CEA Humanized Chimeric Antibody:

In ELISA experiment, CEA, goat-anti-human κ chain (Sigma), or goat-anti-human IgG polyclonal antibody (Sigma) were used for coating the ELISA plates, and goat-antihuman IgG Fc fragment-HRP (Sigma) was used as ELISA antibody. The ELISA results (table 4) indicated that, purified anti-CEA humanized chimeric antibody exhibited strong positive reaction, while the parent mouse monoclonal antibody of anti-CEA humanized chimeric antibody monoclonal antibody exhibited negative reaction. This demonstrated that the purified anti-CEA humanized chimeric antibody contained the light chain and heavy chain constant regions of human IgG.

TABLE 4

Using ELISA to examine the humanized property of anti-CEA humanized chimeric antibody

| Sample (100 ng/ml) | $OD_{490}^a$ | $OD_{490}^b$ | $OD_{490}^c$ |
|---|---|---|---|
| anti-CEA humanized chimeric antibody | 2.361 ± 0.127 | 2.870 ± 0.204 | 2.570 ± 0.169 |
| parent mouse monoclonal antibody | 0.074 ± 0.000 | 0.072 ± 0.008 | 0.074 ± 0.005 |
| human IgG1 | 0.072 ± 0.007 | 2.887 ± 0.186 | 2.565 ± 0.198 |
| PBS | 0.072 ± 0.005 | 0.070 ± 0.007 | 0.070 ± 0.007 |

$^a$CEA was used for coating;
$^b$goat-anti-human IgG was used for coating;
$^c$goat-anti-human κ chain was used for coating.

Western-blotting experiment was performed, wherein reductive SDS-PAGE was conducted for the anti-CEA humanized chimeric antibody. After the antibody was transfer onto the membrane, goat-anti-human IgG Fc fragment-HRP or goat-anti-human κ chain polyclonal antibody were used to respectively conduct Western-blotting. The results (FIG. 11) indicated that, the protein band at 55 kD can be recognized by goat-anti-human IgG Fc fragment-HRP, forming a single specific band that was stained, and the size indicated by the band corresponded to the heavy chain of the antibody. The control mouse monoclonal antibody did not show a band at this position, demonstrating that the expressed anti-CEA humanized chimeric antibody heavy chain contained human constant region. The protein band at 25 kD can be recognized by goat-anti-human κ chain polyclonal antibody, presenting a single specific band that was stained, and the size indicated by this band corresponded to the light chain of the antibody. The control mouse monoclonal antibody exhibited negative reaction here, indicating that anti-CEA humanized chimeric antibody contained human κ chain constant region.

Goat-anti-human IgG, goat-anti-human IgM and goat-anti-human IgA were used to immunize serum, double immuno-diffusion test was used for the examination. The results indicted that the anti-CEA humanized chimeric antibody belonged to immunoglobulin of human IgG type. Mouse-anti-human IgG1, mouse-anti-human IgG2, mouse-anti-human IgG3, and mouse-anti-human IgG4 monoclonal antibody were used to conduct ELISA test, and the results indicated that the anti-CEA humanized chimeric antibody was human IgG1.

3. Identification of the In Vivo Targeting Property of the Anti-CEA Humanized Chimeric Antibody:

Several in vivo radioactive immuno-experiments were performed, including in vivo radioactive immuno-uptake experiment, in vivo radioactive immuno-biodistribution experiment, so as to examine the anti-CEA humanized chimeric antibody for the property of specifically targeting tumors in vivo (mice carrying tumors of CEA positive tumor colon cancer cell LS174T were used as model). The results indicated that, after the injection of nuclide $^{125}$I labeled anti-CEA humanized chimeric antibody, the tumors uptook the most labeled antibody among all the tissues, much higher than other normal tissues, which can reach up to 33% at most, and 26% can remain after 7d. The labeled antibody can well accumulate in the tumors and can remain for a long time. The uptake amounts in normal tissues were low, and they did not remain and all rapidly decreased as time went on (FIG. 12); the results of T/N ratio study showed that the labeled antibody mainly distributed in tumors 24 hours after being injected, and a little of them distributed in blood pool. But 96 hours later, it predominantly distributed in tumors only, showing that nuclide labeled anti-CEA humanized chimeric antibody can specifically distribute in the tumors, but not in normal tissues (FIG. 13). The above results indicated that, anti-CEA humanized chimeric antibody had excellent in vivo tumor targeting property, and can specifically bind to CEA positive tumor cells in animals, so as to specifically accumulate and remain in the tumors, while it did not distribute or remain in normal tissues other than blood pool.

Example 7

Preparation of Diagnostic Medicament for In Vivo Radioactive Immuno-Imaging Diagnosis Using Anti-CEA Humanized Chimeric Antibody In vivo radioactive immuno-imaging experiments were adopted to evaluate the potency of the diagnostic medicament (prepared using the anti-CEA humanized chimeric antibody of the invention) for in vivo radioactive immuno-imaging diagnosis. The results as shown in FIG. 14 indicated that, 24 hours after the injection of nuclide $^{188}$Re labeled anti-CEA humanized chimeric antibody of the invention, the tumors can be clearly imaged. The tumors became even clearer after 5-7 days, and the size of the smallest tumor that can be imaged was 0.5 cm. The results indicate very good application potential for in vivo diagnosis.

Example 8

Preparation of Therapeutic Medicament for In Vivo Radioactive Immuno-Therapy of CEA Positive Tumors Using Anti-CEA Humanized Chimeric Antibody Nuclide I-131 was used to label the anti-CEA humanized chimeric antibody (abbreviated as rch24, about 20 mCi/mg protein). The efficacy of in vivo radioactive immuno-therapy for killing colon cancer tumors was studied in mice carrying transplanted tumors of human CEA positive colon cancer cell LS180 (purchased from ATCC, USA), wherein one million of the LS180 were s.c. injected to the back of the right side of said mice, and the therapies were conducted after the size of the tumors were appropriate. The results indicated that, as for the formed tumors (therapies were conducted after the size of the tumors were over 0.5 cm$^3$), single therapy using 250 µCi/dose of labeled antibodies with high immunoactivity and specific radioactivity showed a tumor inhibition rate of 81.1% for the formed tumors (table 5, FIG. 15); while for the therapy group in which 125 µCi/mouse was administered 3 times with 1 w interval (therapies were conducted when the size of the tumors were about 0.1 cm$^3$), the tumor inhibition rate was 93% (table 6, FIG. 16), and the growth of the tumors was almost stopped. In both cases the growth of human colon cancer can be significantly inhibited. Haemogram analysis and preliminary toxicology study for the variation of body weight indicated that, when using $^{131}$I labeled anti-CEA humanized chimeric antibody for in vivo radioactive immuno-therapy of human colon cancer, each components in the haemogram and the body weight of mice were not significantly different between the therapy group and the control group, demonstrating that it has no apparent toxicity.

TABLE 5

The tumor inhibition rate of single therapy using 250 µCi/dose
against formed tumors was 81.1%

| Groups | Number | Average tumor weight (X ± SD, g) | Inhibition rate (%) | P value |
|---|---|---|---|---|
| PBS | 6 | 4.048 ± 2.428 | — | |
| hIgG | 6 | 3.859 ± 1.928 | — | |
| rch24 | 6 | 0.765 ± 0.442 | 81.1 | <0.038 |

TABLE 6

The tumor inhibition rate of 3-dose-therapy using 125 µCi/dose labeled
antibody was 93%

| Groups | Dose | Tumor weight (X ± SD, g) | Inhibition rate (%) | P value |
|---|---|---|---|---|
| hIgG | 150 µCi/mouse × 3 | 8.18 ± 6.13 | — | |
| rch24 | 150 µCi/mouse × 3 | 0.57 ± 0.47 | 93.04 | <0.05 |

In naked mice model carrying human large intestine cancer, the in vivo anti-tumor activity of the tested sample (i.e. 131I labeled anti-CEA chimeric antibody rch24) was observed. Method: 8-10 days after human large intestine cancer cells LS180, LS174T, and SW1116 were respectively s.c. inoculated to BABL/c nu/nu naked mouse, different groups were respectively administered. Based on a balanced principle according to the size of tumors, the groups were divided as: control group; "naked" anti-CEA humanized chimeric antibody rch24 groups (156.2 µg/kg group and 625.0 µg/kg group); irrelevant human IgG labeled with identical specific radioactivity groups (3.1 mCi/kg group and 12.5 mCi/kg group); 131I labeled anti-CEA humanized chimeric antibody rch24 groups (3.1 mCi/kg group, 6.25 mCi/kg group and 12.5 mCi/kg group); and positive chemotherapy medicament control group. The tested samples and relevant control samples were administered through injection in caudal vein, once every ten days, and twice in total. In a regular manner, the general conditions of animals were observed, the body weight was measured, the sizes of tumors were measured, the serum CEA level and peripheral blood index were measured, and the distribution of isotopes in tumor tissues and non-tumor tissues were determined. The naked mice carrying tumors were sacrificed at the end of the experiment and the weights of tumors were measured. Results: one naked mouse died in the high dose group of tested sample (131I labeled anti-CEA chimeric antibody rch24), and one naked mouse died in the high dose group of irrelevant human IgG labeled with identical specific radioactivity. After administration, in all the groups of the tested sample, the sizes of tumors were smaller than those of the control group, and the relative tumor proliferation rate were lower than that of the control group. The tumor inhibition rate for the three tumor strains LS180, LS174, SW1116 was 47.8-71.4% in low dose group, 52.2-75.0% in moderate dose group, and 65.2-86.2% in high dose group. The serum CEA levels of naked mice in all the groups of the tested sample were clearly lower than those of the control group. When compared with different dose groups of the "naked" anti-CEA humanized chimeric antibody and of the 131I labeled irrelevant human IgG the tumor inhibition effects were more significant in corresponding groups of the tested sample. As for the tumor inhibition effect for the three tumor strains, the tested sample 131I labeled anti-CEA chimeric antibody rch24 was most potent for inhibiting the growth of LS180 tumors. 48 hours and 96 hours after the first administration, the distribution of isotopes in tumor tissues were clearly higher than that in the non-tumor tissues. 30 days after the administration, indexes like peripheral blood leukocytes count etc. in the naked mice of administration group were not significantly different to that of the control group. Conclusion: the tested sample 131I labeled anti-CEA chimeric antibody rch24 can significantly inhibit the growth of the human large intestine cancer carried in mice in a dosage-dependent manner, and can simultaneously decrease the serum CEA level in naked mice carrying tumors, and the targeted distribution thereof in tumor tissues was significant. The administration was conducted twice with a ten-day interval, and after 30 days the hematogenesis function of the naked mice carrying tumors in the administered group was not clearly changed.

TABLE 7 the effect of $^{131}$I labeled anti-CEA chimeric antibody on tumor weight,
and the tumor inhibiting rate in naked mice carrying tumors
(LS180, batch 1)

| Group | tumor weight (g) | tumor inhibiting rate (%) |
|---|---|---|
| control group | 2.8 ± 0.8 | — |
| rch24 low dose group | 1.7 ± 0.5* | 39.3 |
| rch24 high dose group | 1.4 ± 0.3** | 50.0 |
| human IgG low dose group | 1.1 ± 0.2*** | 60.7 |
| human IgG high dose group | 1.9 ± 0.2*** | 67.9 |
| 3.1 mCi/kg group | 0.8 ± 0.2*** | 71.4 |
| 6.25 mCi/kg group | 0.7 ± 0.2***###&& | 75.0 |
| 12.5 mCi/kg group | 0.4 ± 0.1***$$$@@@!! | 85.7 |
| positive control group | 1.6 ± 0.3** | 42.9 |

Note:
as compared with control group, *p < 0.05, p < 0.01, *p < 0.001;
as compared with rch24 low dose group, #p < 0.05, ##p < 0.01;
as compared with rch24 high dose group, $$$p < 0.001;
as compared with IgG low dose group, &&p < 0.01;
as compared with IgG high dose group, @@@p < 0.001;
as compared with 6.25 mCi/kg group, !!p < 0.01.

TABLE 8 the effect of $^{131}$I labeled anti-CEA chimeric antibody on tumor weight,
and the tumor inhibiting rate in naked mice carrying tumors
(LS180, batch 2)

| Group | tumor weight (g) | tumor inhibiting rate (%) |
|---|---|---|
| model control group | 2.9 ± 0.6 | — |
| rch24 low dose group | 1.8 ± 0.2*** | 37.9 |
| rch24 high dose group | 1.5 ± 0.1*** | 48.3 |
| human IgG low dose group | 1.2 ± 0.1*** | 58.6 |
| human IgG high dose group | 1.0 ± 0.2*** | 65.5 |
| 3.1 mCi/kg group | 0.9 ± 0.3*** | 69.0 |
| 6.25 mCi/kg group | 0.8 ± 0.1***###&&& | 72.4 |
| 12.5 mCi/kg group | 0.4 ± 0.1***$$$@@@!!! | 86.2 |
| positive control group | 1.7 ± 0.2*** | 41.4 |

Note:
as compared with model control group, ***p < 0.001;
as compared with rch24 low dose group, ###p < 0.001;
as compared with rch24 high dose group, $$$p < 0.001;
as compared with IgG low dose group, &&&p < 0.001;
as compared with IgG high dose group, @@@p < 0.001;
as compared with 6.25 mCi/kg group, !!!p < 0.001.

TABLE 9 the effect of $^{131}$I labeled anti-CEA chimeric antibody on tumor weight, and the tumor inhibiting rate in naked mice carrying tumors (LS174T, batch 1)

| Group | tumor weight (g) | tumor inhibiting rate (%) |
|---|---|---|
| model control group | 2.5 ± 0.2 | — |
| rch24 low dose group | 1.6 ± 0.3*** | 36.0 |
| rch24 high dose group | 1.3 ± 0.2*** | 48.0 |
| human IgG low dose group | 1.1 ± 0.2*** | 56.0 |
| human IgG high dose group | 1.0 ± 0.1*** | 60.0 |
| 3.1 mCi/kg group | 0.9 ± 0.1*** | 64.0 |
| 6.25 mCi/kg group | 0.7 ± 0.1***###&&&% | 72.0 |
| 12.5 mCi/kg group | 0.5 ± 0.1***$$$@@@ | 80.0 |
| positive control group | 1.4 ± 0.2*** | 44.0 |

Note:
as compared with model control group, ***$p < 0.001$;
as compared with rch24 low dose group, ###$p < 0.001$;
as compared with rch24 high dose group, $$$$p < 0.001$;
as compared with IgG low dose group, &&&$p < 0.001$,
as compared with 3.1 mCi/kg group, %$p < 0.05$;
as compared with IgG high dose group, @@@$p < 0.001$.

TABLE 10 the effect of $^{131}$I labeled anti-CEA chimeric antibody on tumor weight, and the tumor inhibiting rate in naked mice carrying tumors (LS174T, batch 2)

| Group | tumor weight (g) | tumor inhibiting rate (%) |
|---|---|---|
| model control group | 2.6 ± 0.2 | — |
| rch24 low dose group | 1.7 ± 0.2*** | 34.6 |
| rch24 high dose group | 1.5 ± 0.1*** | 42.3 |
| human IgG low dose group | 1.3 ± 0.1*** | 50.0 |
| human IgG high dose group | 1.1 ± 0.1***### | 57.7 |
| 3.1 mCi/kg group | 1.0 ± 0.1***### | 61.5 |
| 6.25 mCi/kg group | 0.8 ± 0.1***###&&&% | 69.2 |
| 12.5 mCi/kg group | 0.7 ± 0.1***$$$@@@! | 73.1 |
| positive control group | 1.4 ± 0.2*** | 46.2 |

Note:
as compared with model control group, ***$p < 0.001$;
as compared with rch24 low dose group, ###$p < 0.001$;
as compared with rch24 high dose group, $$$$p < 0.001$;
as compared with IgG low dose group, &&&$p < 0.001$;
as compared with 3.1 mCi/kg group, %$p < 0.05$;
as compared with IgG high dose group, @@@$p < 0.001$;
as compared with 6.25 mCi/kg group, !$p < 0.05$.

TABLE 11 the effect of $^{131}$I labeled anti-CEA chimeric antibody on tumor weight, and the tumor inhibiting rate in naked mice carrying tumors (SW1116, batch 1)

| Group | tumor weight (g) | tumor inhibiting rate (%) |
|---|---|---|
| model control group | 2.2 ± 0.1 | — |
| rch24 low dose group | 1.6 ± 0.2*** | 27.3 |
| rch24 high dose group | 1.4 ± 0.2*** | 36.4 |
| human IgG low dose group | 1.2 ± 0.2*** | 45.5 |
| human IgG high dose group | 1.0 ± 0.1*** | 54.5 |
| 3.1 mCi/kg group | 0.9 ± 0.2*** | 59.1 |
| 6.25 mCi/kg group | 0.8 ± 0.2***###&& | 63.6 |
| 12.5 mCi/kg group | 0.7 ± 0.1***$$$@@@ | 68.2 |
| positive control group | 1.5 ± 0.2*** | 31.8 |

Note:
as compared with model control group, ***$p < 0.001$;
as compared with rch24 low dose group, ###$p < 0.001$;
as compared with rch24 high dose group, $$$$p < 0.001$;
as compared with IgG low dose group, &&$p < 0.01$;
as compared with IgG high dose group, @@@$p < 0.001$.

TABLE 12 the effect of $^{131}$I labeled anti-CEA chimeric antibody on tumor weight, and the tumor inhibiting rate in naked mice carrying tumors (SW1116, batch 2)

| Group | tumor weight(g) | tumor inhibiting rate (%) |
|---|---|---|
| model control group | 2.3 ± 0.1 | — |
| rch24 low dose group | 1.7 ± 0.2*** | 26.1 |
| rch24 high dose group | 1.5 ± 0.2*** | 34.8 |
| human IgG low dose group | 1.4 ± 0.1*** | 39.1 |
| human IgG high dose group | 1.3 ± 0.3*** | 43.5 |
| 3.1 mCi/kg group | 1.2 ± 0.1*** | 47.8 |
| 6.25 mCi/kg group | 1.1 ± 0.1***###&&& | 52.2 |
| 12.5 mCi/kg group | 0.8 ± 0.1***$$$@@@!! | 65.2 |
| positive control group | 1.5 ± 0.2*** | 34.8 |

Note:
as compared with model control group, ***$p < 0.001$;
as compared with rch24 low dose group, ###$p < 0.001$;
as compared with rch24 high dose group, $$$$p < 0.001$;
as compared with IgG low dose group, &&&$p < 0.001$;
as compared with IgG high dose group, @@@$p < 0.001$;
as compared with 6.25 mCi/kg group, !!$p < 0.01$.

---

The invention claimed is:

1. A chimeric monoclonal antibody, wherein the monoclonal antibody comprises a heavy chain comprising CDR regions in sequence as set forth in SEQ ID NOs: 7-9, and a light chain comprising CDR regions in sequence as set forth in SEQ ID NOs: 10-12, wherein the monoclonal antibody can specifically bind to carcinoembryonic antigen, and wherein the chimeric monoclonal antibody is produced from the cell line deposited as CGMCC No. 3803.

2. The antibody according to claim 1, wherein said antibody comprises a heavy chain having the amino acid sequence of SEQ ID NO: 1 and a light chain having the amino acid sequence of SEQ ID NO:2.

3. A nucleic acid comprising a polynucleotide encoding the chimeric antibody according to claim 1, or a complementary sequence thereof.

4. The nucleic acid according to claim 3, which is DNA or RNA.

5. An expression vector comprising a polynucleotide encoding the amino acid sequence of SEQ ID NO: 1 and SEQ ID NO:2.

6. A host cell comprising the nucleic acid according to claim 3, or comprising the vector according to claim 5.

* * * * *

SEQUENCE LISTING

```
<160> NUMBER OF SEQ ID NOS: 17

<210> SEQ ID NO 1
<211> LENGTH: 450
<212> TYPE: PRT
<213> ORGANISM: Artificial
<220> FEATURE:
<223> OTHER INFORMATION: chimeric

<400> SEQUENCE: 1

Gln Val Gln Leu Gln Gln Ser Gly Ala Glu Leu Val Arg Ser Gly Ala
1               5                   10                  15

Ser Ile Lys Leu Ser Cys Thr Ala Ser Gly Phe Asn Ile Lys His Tyr
            20                  25                  30

Tyr Met His Trp Val Lys Gln Arg Pro Glu Gln Gly Leu Glu Trp Ile
        35                  40                  45
```

```
Gly Trp Ile Asn Pro Glu Asn Val Asp Thr Glu Tyr Ala Pro Lys Phe
 50                  55                  60
Gln Gly Lys Ala Thr Met Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
                 85                  90                  95
Asn His Tyr Arg Tyr Ala Gly Gly Ala Leu Asp Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
450
```

```
<210> SEQ ID NO 2
<211> LENGTH: 212
<212> TYPE: PRT
<213> ORGANISM: Artificial
<220> FEATURE:
<223> OTHER INFORMATION: chimeric

<400> SEQUENCE: 2

Asp Ile Gln Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Ile
            20                  25                  30

His Trp Tyr Gln Gln Lys Ser Gly Thr Ser Pro Lys Arg Trp Val Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Asn Asn Asn Pro Tyr Ser
                85                  90                  95

Phe Gly Gly Gly Thr Lys Val Val Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 3
<211> LENGTH: 24
<212> TYPE: DNA
<213> ORGANISM: Artificial
<220> FEATURE:
<223> OTHER INFORMATION: primer

<400> SEQUENCE: 3
gacattcagc tgacccagtc tcca                                          24

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
gttagatctc cagcttggtc cc                                            22

<210> SEQ ID NO 5
<211> LENGTH: 22
<212> TYPE: DNA
```

```
<213> ORGANISM: artificial
<220> FEATURE:
<223> OTHER INFORMATION: primer

<400> SEQUENCE: 5
aggtsmarct gcagsagtcw gg                                              22

<210> SEQ ID NO 6
<211> LENGTH: 34
<212> TYPE: DNA
<213> ORGANISM: Artificial
<220> FEATURE:
<223> OTHER INFORMATION: primer

<400> SEQUENCE: 6
tgaggagacg gtgaccgtgg tcccttggcc ccag                                 34

<210> SEQ ID NO 7
<211> LENGTH: 5
<212> TYPE: PRT
<213> ORGANISM: Mus musculus

<400> SEQUENCE: 7

His Tyr Tyr Met His
1               5

<210> SEQ ID NO 8
<211> LENGTH: 17
<212> TYPE: PRT
<213> ORGANISM: Mus musculus

<400> SEQUENCE: 8

Trp Ile Asn Pro Glu Asn Val Asp Thr Glu Tyr Ala Pro Lys Phe Gln
1               5                   10                  15

Gly

<210> SEQ ID NO 9
<211> LENGTH: 11
<212> TYPE: PRT
<213> ORGANISM: Mus musculus

<400> SEQUENCE: 9

Tyr Arg Tyr Ala Gly Gly Gly Ala Leu Asp Tyr
1               5                   10

<210> SEQ ID NO 10
<211> LENGTH: 10
<212> TYPE: PRT
<213> ORGANISM: Mus musculus

<400> SEQUENCE: 10

Ser Ala Ser Ser Ser Val Ser Tyr Ile His
1               5                   10

<210> SEQ ID NO 11
<211> LENGTH: 7
<212> TYPE: PRT
<213> ORGANISM: Mus musculus

<400> SEQUENCE: 11

Asp Thr Ser Lys Leu Ala Ser
1               5

<210> SEQ ID NO 12
```

<211> LENGTH: 9
<212> TYPE: PRT
<213> ORGANISM: Mus musculus

<400> SEQUENCE: 12

Gln Gln Trp Asn Asn Asn Pro Tyr Ser
1               5

<210> SEQ ID NO 13
<211> LENGTH: 64
<212> TYPE: DNA
<213> ORGANISM: Artificial
<220> FEATURE:
<223> OTHER INFORMATION: Primer

<400> SEQUENCE: 13
gggtccaagc ttgcggccgc aactgaggaa gcaaagttta aattctactc acgtttgatc     60
acca                                                                 64

<210> SEQ ID NO 14
<211> LENGTH: 40
<212> TYPE: DNA
<213> ORGANISM: Artificial
<220> FEATURE:
<223> OTHER INFORMATION: Primer

<400> SEQUENCE: 14
gctcgggaat tcggatccat gggatggagc tgtatcatcc                           40

<210> SEQ ID NO 15
<211> LENGTH: 41
<212> TYPE: DNA
<213> ORGANISM: Artificial
<220> FEATURE:
<223> OTHER INFORMATION: Primer

<400> SEQUENCE: 15
gggtccgaat tcgcggccgc tataaatctc tggccatgaa g                         41

<210> SEQ ID NO 16
<211> LENGTH: 315
<212> TYPE: DNA
<213> ORGANISM: Artificial
<220> FEATURE:
<223> OTHER INFORMATION: VL

<400> SEQUENCE: 16
gacatccagc tgacccagtc tccagcaatc atgtctgcat ctccagggga gaaggtcacc     60
atgacctgca gtgccagctc aagtgtaagt tacatacact ggtatcagca gaagtcaggc    120
acctccccca aaagatgggt ttatgacaca tccaaactgg cttctggagt ccctgctcgc    180
ttcagtggca gtgggtctgg gacctcttac tctctcacaa tcagcaccat ggaggctgaa    240
gatgctgcca cttattactg ccagcagtgg aataataacc catacacgtt cggagggggg    300
accaaggtgg agatc                                                    315

<210> SEQ ID NO 17
<211> LENGTH: 360
<212> TYPE: DNA
<213> ORGANISM: Artificial
<220> FEATURE:
<223> OTHER INFORMATION: VH

<400> SEQUENCE: 17

```
caggtccaac tgcagcagtc tggggcagaa cttgtgaggt caggggcctc aatcaagttg        60
tcctgcacag cttctggctt caacattaaa cactactata tgcactgggt gaaacagagg       120
cctgaacagg gcctggagtg gattggatgg attaatcctg agaatgttga tactgaatat       180
gcccccaagt tccagggcaa ggccactatg actgcagaca catcctccaa cacagcctac       240
ctgcagctca gcagcctgac atctgaggac actgccgtct attactgtaa tcactatagg       300
tacgccggag ggggtgcttt ggactactgg ggccaaggga ccacggtcac cgtctcctca       360
```